United States Patent
Mekalanos et al.

(10) Patent No.: US 9,833,503 B2
(45) Date of Patent: Dec. 5, 2017

(54) METHODS FOR DISPLAYING POLYPEPTIDES AND USES THEREOF

(71) Applicant: PRESIDENT AND FELLOWS OF HARVARD COLLEGE, Cambridge, MA (US)

(72) Inventors: John Mekalanos, Brighton, MA (US); Marek Basler, Prague (CZ)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/380,004

(22) PCT Filed: Feb. 22, 2013

(86) PCT No.: PCT/US2013/027211
§ 371 (c)(1),
(2) Date: Aug. 20, 2014

(87) PCT Pub. No.: WO2013/126622
PCT Pub. Date: Aug. 29, 2013

(65) Prior Publication Data
US 2015/0132334 A1    May 14, 2015

Related U.S. Application Data

(60) Provisional application No. 61/602,913, filed on Feb. 24, 2012.

(51) Int. Cl.
| | |
|---|---|
| *A61K 39/02* | (2006.01) |
| *C12N 15/10* | (2006.01) |
| *C12N 15/74* | (2006.01) |
| *C07K 14/21* | (2006.01) |
| *C07K 14/28* | (2006.01) |
| *C12N 15/78* | (2006.01) |
| *A61K 39/00* | (2006.01) |

(52) U.S. Cl.
CPC ............ *A61K 39/107* (2013.01); *C07K 14/21* (2013.01); *C07K 14/28* (2013.01); *C12N 15/1037* (2013.01); *C12N 15/74* (2013.01); *C12N 15/78* (2013.01); *A61K 39/00* (2013.01); *A61K 2039/64* (2013.01); *C07K 2319/10* (2013.01)

(58) Field of Classification Search
None
See application file for complete search history.

(56) References Cited

U.S. PATENT DOCUMENTS

| | | |
|---|---|---|
| 5,840,313 A | 11/1998 | Vahlne et al. |
| 5,846,546 A | 12/1998 | Hurwitz et al. |
| 5,876,731 A | 3/1999 | Sia et al. |
| 6,190,669 B1 | 2/2001 | Noriega et al. |
| 2011/0150841 A1 | 6/2011 | Mougous et al. |

OTHER PUBLICATIONS

Bonemann, et al (Molecular Microbiology (2010), 76(4), 815-821).*
Ghosh et al. "Induction of HLA-A2-restricted CTL responses by a tubular structure carrying human melanoma epitopes." Vaccine, vol. 20, No. 19-20, Jun. 7, 2002, pp. 2463-2473.
Ghosh et al. "Induction of protective antiviral cytotoxic T cells by a tubular structure capable of carrying large foreign sequences." Vaccine, vol. 20, No. 9-10, Jan. 31, 2002, pp. 1369-1377.
Bonemann et al. "Remodelling of VipA/VipB tubules by ClpV-mediated threading is crucial for type VI protein secretion." The EMBO Journal, vol. 28, 2009, pp. 315-325.
Basler et al., "Type VI secretion requires a dynamic contractile phage tail-like structure." Nature. 483(7388):182-6 (2012).
Das & Chaudhuri., "Identification of a unique IAHP (IcnnF associated homologous proteins) cluster in Vibrio cholerae and other proteobacteria through in silico analysis." In Silico Biol. 3(3):287-300 (2003).
Guenaga et al., "Heterologous epitope-scaffold prime:boosting immuno-focuses B cell responses to the HIV-1 gp41 2F5 neutralization determinant." PloS ONE 6(1):e16074 (2011).
Guzman et al.,"Tight regulation, modulation, and high-level expression by vectors containing the arabinose PBAD promoter." J Bacteriol. 177(14):4121-30 (1995).
Leiman et al., "Type VI secretion apparatus and phage tail-associated protein complexes share a common evolutionary origin." PNAS 106(11):4154-9 (2009).
Pietrosiuk et al., "Molecular basis for the unique role of the AAA+ chaperone ClpV in type VI protein secretion." J Biol Chem. 286(34):30010-21 (2011).

* cited by examiner

*Primary Examiner* — Jennifer Graser
(74) *Attorney, Agent, or Firm* — Mark J. FitzGerald; Teresa A. Ptashka; Nixon Peabody LLP

(57) ABSTRACT

Provided herein are methods and compositions for displaying a polypeptide on a tubular structure and uses of such displayed polypeptides in the production of antibodies or vaccines.

6 Claims, 17 Drawing Sheets

SEQUENCE LISTING

```
<160> NUMBER OF SEQ ID NOS: 17

<210> SEQ ID NO 1
<211> LENGTH: 168
<212> TYPE: PRT
<213> ORGANISM: Vibrio cholerae

<400> SEQUENCE: 1

Met Ser Lys Glu Gly Ser Val Ala Pro Lys Glu Arg Ile Asn Ile Lys
1               5                   10                  15

Tyr Ile Pro Ala Thr Gly Asp Ala Gln Ala Glu Val Glu Leu Pro Leu
            20                  25                  30

Lys Thr Leu Val Val Gly Asp Phe Lys Gly His Ala Glu Gln Thr Pro
        35                  40                  45

Leu Glu Glu Arg Ala Thr Val Thr Val Asp Lys Asn Asn Phe Glu Ala
    50                  55                  60

Val Met Arg Glu Ser Glu Leu Lys Ile Thr Ala Thr Val Lys Asn Lys
65                  70                  75                  80

Leu Thr Asp Asp Glu Asn Ala Glu Leu Pro Val Glu Leu Asn Phe Lys
                85                  90                  95

Ser Leu Ala Asp Phe Ala Pro Asp Ala Val Ala Ser Gln Val Pro Glu
            100                 105                 110

Leu Lys Lys Leu Ile Glu Leu Arg Glu Ala Leu Val Ala Leu Lys Gly
        115                 120                 125

Pro Leu Gly Asn Ile Pro Ala Phe Arg Glu Arg Leu Gln Ser Leu Leu
    130                 135                 140

Asn Ser Glu Glu Ser Arg Glu Lys Leu Leu Ala Glu Leu Asn Leu Leu
145                 150                 155                 160

Ser Gly Gln Glu Glu Pro Gln Ala
                165

<210> SEQ ID NO 2
<211> LENGTH: 507
<212> TYPE: DNA
<213> ORGANISM: Vibrio cholerae

<400> SEQUENCE: 2
atgtctaaag aaggaagtgt agctcccaaa gagcggatta atatcaagta tattccggcg      60 acggggatg cacaggctga ggttgagcta ccactcaaaa ccctagttgt aggtgatttc      120
aaagggcatg cggagcaaac cccattggaa gagcgtgcaa cagtcacggt agataagaac      180
aactttgaag ccgtaatgcg cgagagcgag ctgaaaatca ccgccacggt gaaaaacaag      240
ctgactgatg atgagaatgc cgagcttcct gttgaactca atttcaaatc cttagccgac      300
ttcgctcctg atgcggtggc atcacaagtt ccagaactga aaaaattgat tgagttgcgt      360
gaagcgttag ttgcccttaa agggccgcta ggcaacattc ccgcatttcg tgagcgttta      420
cagtcattac tcaactcaga agagtcgaga gaaaagctgt tggcagaact gaatctgctc      480
agtggtcaag aagagccaca agcgtaa                                         507
```

<210> SEQ ID NO 3
<211> LENGTH: 492
<212> TYPE: PRT
<213> ORGANISM: Vibrio cholerae

<400> SEQUENCE: 3

```
Met Met Ser Thr Thr Glu Lys Val Leu Glu Arg Pro Gln Leu Ala Gln
1               5                   10                  15

Gly Ser Leu Leu Asp Glu Ile Met Ala Gln Thr Arg Ile Ala Pro Ser
            20                  25                  30

Glu Glu Gly Tyr Asp Ile Ala Lys Lys Gly Val Ala Ala Phe Ile Glu
        35                  40                  45

Asn Leu Met Gly Ser Gln His Ser Ala Glu Pro Val Asn Lys Ser Leu
    50                  55                  60

Val Asp Gln Met Leu Val Glu Leu Asp Lys Lys Ile Ser Ala Gln Met
65                  70                  75                  80

Asp Glu Ile Leu His Asn Ser Gln Phe Gln Ala Met Glu Ser Ala Trp
                85                  90                  95

Arg Gly Leu Lys Leu Phe Val Asp Arg Thr Asp Phe Arg Glu Asn Asn
            100                 105                 110

Lys Val Glu Ile Leu His Val Thr Lys Asp Glu Leu Leu Glu Asp Phe
        115                 120                 125

Glu Phe Ala Pro Glu Thr Ala Gln Ser Gly Leu Tyr Lys His Val Tyr
    130                 135                 140

Ser Ala Gly Tyr Gly Gln Phe Gly Gly Glu Pro Val Gly Ala Ile Ile
145                 150                 155                 160

Gly Asn Tyr Ala Phe Thr Pro Ser Thr Pro Asp Met Lys Leu Leu Gln
                165                 170                 175

Tyr Met Gly Ala Leu Gly Ala Met Ala His Ala Pro Phe Ile Ser Ser
            180                 185                 190

Val Gly Pro Glu Phe Phe Gly Ile Asp Ser Phe Glu Glu Leu Pro Asn
        195                 200                 205

Ile Lys Asp Leu Lys Ser Thr Phe Glu Ser Pro Lys Tyr Thr Lys Trp
    210                 215                 220

Arg Ser Leu Arg Glu Ser Glu Asp Ala Arg Tyr Leu Gly Leu Thr Ala
225                 230                 235                 240

Pro Arg Phe Leu Leu Arg Val Pro Tyr Asp Pro Ile Glu Asn Pro Val
                245                 250                 255

Lys Ser Phe Asn Tyr Ala Glu Asn Val Ser Ala Ser His Glu His Tyr
            260                 265                 270

Leu Trp Gly Asn Thr Ala Phe Ala Phe Ala Thr Arg Leu Thr Asp Ser
        275                 280                 285

Phe Ala Lys Tyr Arg Trp Cys Pro Asn Ile Ile Gly Pro Gln Ser Gly
    290                 295                 300

Gly Ala Val Glu Asp Leu Pro Val His Val Phe Glu Ser Met Gly Ala
305                 310                 315                 320

Leu Gln Ser Lys Ile Pro Thr Glu Val Leu Ile Thr Asp Arg Lys Glu
                325                 330                 335

Phe Glu Leu Ala Glu Gly Phe Ile Ala Leu Thr Met Arg Lys Gly
            340                 345                 350

Ser Asp Asn Ala Ala Phe Phe Ser Ala Asn Ser Ile Gln Lys Pro Lys
        355                 360                 365

Val Phe Pro Asn Thr Lys Glu Gly Lys Glu Ala Glu Thr Asn Tyr Lys
    370                 375                 380
```

```
Leu Gly Thr Gln Leu Pro Tyr Met Met Ile Ile Asn Arg Leu Ala His
385                 390                 395                 400

Tyr Val Lys Val Leu Gln Arg Glu Gln Ile Gly Ala Trp Lys Glu Arg
                405                 410                 415

Gln Asp Leu Glu Arg Glu Leu Asn Ser Trp Ile Lys Gln Tyr Val Ala
            420                 425                 430

Asp Gln Glu Asn Pro Pro Ala Asp Val Arg Ser Arg Pro Leu Arg
        435                 440                 445

Ala Ala Arg Ile Glu Val Met Asp Val Glu Gly Asn Pro Gly Trp Tyr
    450                 455                 460

Gln Val Ser Leu Ser Val Arg Pro His Phe Lys Tyr Met Gly Ala Asn
465                 470                 475                 480

Phe Glu Leu Ser Leu Val Gly Arg Leu Asp Gln Ala
                485                 490
```

```
<210> SEQ ID NO 4
<211> LENGTH: 1479
<212> TYPE: DNA
<213> ORGANISM: Vibrio cholerae

<400> SEQUENCE: 4
```

| | |
|---|---|
| atgatgtcta cgactgaaaa ggtattggaa aggccacagc ttgctcaagg cagccttctt | 60 |
| gatgaaatta tggcgcaaac ccgtatcgca ccaagcgaag agggttacga catcgcgaaa | 120 |
| aaaggtgttg cagcgtttat cgaaaatctt atgggttcac aacactctgc tgagcctgtc | 180 |
| aacaaatctc tggttgacca atgttggtt gaactggata aaaaaatcag tgcacagatg | 240 |
| gatgaaatcc tgcacaactc acaattccaa gcgatggaat cggcgtggcg cggtttgaag | 300 |
| ctgttcgtgg atcgcactga ttttcgtgaa aataacaaag tcgaaatcct tcacgtaacc | 360 |
| aaagatgaac tgctggaaga tttcgagttt gctccagaaa cggctcagtc cggtctttac | 420 |
| aagcacgttt attctgccgg ttatggtcaa tttggtggcg aacctgttgg cgcgatcatt | 480 |
| ggtaactatg cgtttacccc ttcaacgcca gatatgaagc tgctgcaata catgggcgca | 540 |
| ctgggtgcca tggcgcatgc tccttctcatt tcaagcgtag gtcctgaatt ctttggtatc | 600 |
| gactccttcg aagaactgcc taacattaaa gatctcaagt cgacatttga agcccgaaa | 660 |
| tacaccaaat ggcgttcact gcgtgaatcg gaagatgctc gctatcttgg tttgactgcg | 720 |
| cctcgtttcc tgctgcgtgt tccttacgat ccaatcgaaa atccagtgaa gtcgttcaat | 780 |
| tatgcggaaa acgtcagtgc ttcgcacgag cactacctgt ggggtaacac ggcatttgcc | 840 |
| ttcgcaactc gtttgacgga tagctttgct aaatatcgct ggtgtccaaa cattatcggt | 900 |
| ccacaaagtg gtggtgcagt tgaagatctg ccggtgcatg tctttgaatc tatgggtgca | 960 |
| ttgcaaagca agatcccaac cgaagtcctg atcacggacc gtaaagaatt tgaactggcg | 1020 |
| gaagaaggtt ttattgctct tactatgcgt aaaggcagtg ataacgcggc gttcttctct | 1080 |
| gcaaactcca ttcaaaaacc taaggttttc ccaaatacca agaaggcaa agaagcggaa | 1140 |
| accaactaca gttgggtac ccagttgccg tacatgatga tcatcaaccg tttggcgcac | 1200 |
| tatgtgaaag ttctgcaacg tgagcagatc ggtgcttgga agagcgtca agatcttgag | 1260 |
| cgtgaactga actcatggat caaacaatac gttgctgatc aagagaaccc acctgcagac | 1320 |
| gtacgtagcc gtcgtccact tcgtgctgcg cgcattgaag tgatggatgt ggaaggcaat | 1380 |
| ccaggttggt atcaggtgtc gctctcggtt cgtcctcact taagtacat gggtgcgaac | 1440 |
| tttgagttgt cattagttgg acgtcttgat caagcctga | 1479 |

```
<210> SEQ ID NO 5
<211> LENGTH: 20
<212> TYPE: PRT
<213> ORGANISM: Chlamydia trachomatis

<400> SEQUENCE: 5

Asn Val Thr Gln Asp Leu Thr Ser Ser Thr Ala Lys Leu Glu Cys Thr
1               5                   10                  15

Gln Asp Leu Ile
            20

<210> SEQ ID NO 6
<211> LENGTH: 20
<212> TYPE: PRT
<213> ORGANISM: Chlamydia trachomatis

<400> SEQUENCE: 6

Ala Lys Leu Glu Cys Thr Gln Asp Leu Ile Ala Gln Gly Lys Leu Ile
1               5                   10                  15

Val Thr Asn Pro
            20

<210> SEQ ID NO 7
<211> LENGTH: 9
<212> TYPE: PRT
<213> ORGANISM: Chlamydia trachomatis

<400> SEQUENCE: 7

Ser Asn Leu Lys Arg Met Gln Lys Ile
1               5

<210> SEQ ID NO 8
<211> LENGTH: 9
<212> TYPE: PRT
<213> ORGANISM: Chlamydia trachomatis

<400> SEQUENCE: 8

Ala Ala Leu Tyr Ser Thr Glu Asp Leu
1               5

<210> SEQ ID NO 9
<211> LENGTH: 9
<212> TYPE: PRT
<213> ORGANISM: Chlamydia trachomatis

<400> SEQUENCE: 9

Phe Gln Glu Lys Asp Ala Asp Thr Leu
1               5

<210> SEQ ID NO 10
<211> LENGTH: 9
<212> TYPE: PRT
<213> ORGANISM: Chlamydia trachomatis

<400> SEQUENCE: 10

Gln Ser Val Asn Glu Leu Val Tyr Val
1               5

<210> SEQ ID NO 11
<211> LENGTH: 9
<212> TYPE: PRT
<213> ORGANISM: Chlamydia trachomatis
```

```
<400> SEQUENCE: 11

Leu Glu Phe Ala Ser Cys Ser Ser Leu
1               5

<210> SEQ ID NO 12
<211> LENGTH: 9
<212> TYPE: PRT
<213> ORGANISM: Chlamydia trachomatis

<400> SEQUENCE: 12

Ser Gln Ala Glu Gly Gln Tyr Arg Leu
1               5

<210> SEQ ID NO 13
<211> LENGTH: 9
<212> TYPE: PRT
<213> ORGANISM: Chlamydia trachomatis

<400> SEQUENCE: 13

Gly Gln Ser Val Asn Glu Leu Val Tyr
1               5

<210> SEQ ID NO 14
<211> LENGTH: 9
<212> TYPE: PRT
<213> ORGANISM: Chlamydia trachomatis

<400> SEQUENCE: 14

Gln Ala Val Leu Leu Leu Asp Gln Ile
1               5

<210> SEQ ID NO 15
<211> LENGTH: 4
<212> TYPE: PRT
<213> ORGANISM: Human immunodeficiency virus 1

<400> SEQUENCE: 15

Gly Pro Gly Arg
1

<210> SEQ ID NO 16
<211> LENGTH: 14
<212> TYPE: PRT
<213> ORGANISM: Vibrio cholerae

<400> SEQUENCE: 16

Gln Ser Gly Gln Pro Ser Gly Gln Arg Val His Lys Pro Phe
1               5                   10

<210> SEQ ID NO 17
<211> LENGTH: 14
<212> TYPE: PRT
<213> ORGANISM: Vibrio cholerae

<400> SEQUENCE: 17

Met Ser Lys Glu Gly Ser Val Ala Pro Lys Glu Arg Ile Asn
1               5                   10
```

METHODS FOR DISPLAYING POLYPEPTIDES AND USES THEREOF

CROSS REFERENCE TO RELATED APPLICATIONS

This application is a 35 U.S.C. §371 National Phase Entry Application of International Application No. PCT/US2013/27211 filed Feb. 22, 2013, which designates the U.S., and which claims benefit under 35 U.S.C. §119(e) of the U.S. Provisional Application No. 61/602,913, filed Feb. 24, 2012, the content of which is incorporated herein by reference in its entirety.

GOVERNMENT SUPPORT

This invention was made with government support under AI018045 and AI026289 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 14, 2014, is named 002806-073222-US_SL.txt and is 11,093 bytes in size.

FIELD OF THE INVENTION

The field of the invention relates to methods for displaying a polypeptide and uses thereof.

BACKGROUND

Secretion systems allow bacteria to transport macromolecules such as proteins out of effector cells or into either target host cells during pathogenesis or target bacterial cells during competition in various ecological settings. The type 6 secretion systems (T6SS) are encoded by a cluster of 15-20 genes that is present in at least one copy in about 25% of all sequenced Gram-negative bacteria. Although linked to virulence during host infection, recent studies showed that T6SS of *Pseudomonas, Burkholderia* and *Vibrio* species can kill prokaryotic as well as eukaryotic target host cells (Pukatzki, S. et al. *Proc. Natl. Acad. Sci. USA* 103, 1528-1533 (2006); Ma, A. T., et al., *Cell Host Microbe* 5, 234-243 (2009); Russell, A. B. et al. *Nature* 475, 343-347 (2011); MacIntyre, D. L., et al., *Proc. Natl. Acad. Sci. USA* 107, 19520-19524 (2010); Schwarz, S. et al. *PLoS Pathog.* 6, e1001068 (2010); Hood, R. D. et al. *Cell Host Microbe* 7, 25-37 (2010); Zheng, J., *PLoS ONE* 6, e23876 (2011)). T6SS+ bacterial effector cells are thought to kill target cells through translocation of toxic effector proteins in a cell-cell contact-dependent process (Pukatzki, S. et al. *Proc. Natl. Acad. Sci. USA* 103, 1528-1533 (2006); Ma, A. T., et al., *Cell Host Microbe* 5, 234-243 (2009); Russell, A. B. et al. *Nature* 475, 343-347 (2011); Ma, A. T. & Mekalanos, J. J. *Proc. Natl. Acad. Sci. USA* 107, 4365-4370 (2010)). Little is known, however, about how T6SS transport toxic proteins through their own cell membranes or across target cell membranes.

Bioinformatic (Pukatzki, S., *Proc. Natl. Acad. Sci. USA* 104, 15508-15513 (2007)) and structural analyses (Leiman, P. G. et al. *Proc. Natl. Acad. Sci. USA* 106, 4154-4159 (2009); Pell, L. G., *Proc. Natl. Acad. Sci. USA* 106, 4160-4165 (2009)) have indicated that some T6SS components are structural homologues of components present in contractile phage tails. For example, secreted VgrG proteins are structural homologues of the T4 phage needle or spike complex (Pukatzki, S., Ma, et al., *Proc. Natl. Acad. Sci. USA* 104, 15508-15513 (2007); Leiman, P. G. et al. *Proc. Natl. Acad. Sci. USA* 106, 4154-4159 (2009)) and secreted Hcp is a structural homologue of a phage tail tube protein (Leiman, P. G. et al. *Proc. Natl. Acad. Sci. USA* 106, 4154-4159 (2009); Pell, L. G., *Proc. Natl. Acad. Sci. USA* 106, 4160-4165 (2009)). Another highly conserved T6SS gene product is predicted to be a homologue of gp25, a major component of the T4 phage tail base-plate (Leiman, P. G. et al. *Proc. Natl Acad. Sci. USA* 106, 4154-4159 (2009); Leiman, P. G. et al., *Cell* 118, 419-429 (2004); Lossi, N. S., et al. *Microbiology* 157, 3292-3305 (2011)). Two T6SS gene products of *V. cholerae*, VipA and VipB, form tubular structures that can be depolymerized by another T6SS gene product, ClpV (Bonemann, G., et al., *EMBO J.* 28, 315-325 (2009); Pietrosiuk, A. et al. *J. Biol. Chem.* 286, 30010-30021 (2011); Mougous, J. D. et al. *Science* 312, 1526-1530 (2006)). Leiman et al. (Leiman, P. G. et al. *Proc. Natl. Acad. Sci. USA* 106, 4154-4159 (2009)) noted that VipA/VipB tubules visually resemble T4 contracted tail sheath and were the first to propose that a sheath-like structure might power T6SS translocation by a phage tail-like contraction mechanism.

SUMMARY OF THE INVENTION

Provided herein are methods and compositions for displaying a polypeptide on a tubular structure and uses of such displayed polypeptides in the production of antibodies or vaccines.

One aspect provided herein relates to methods for displaying a polypeptide, the method comprising culturing a bacterial cell that expresses a first intracellular tubular protein, and that comprises a construct encoding a polypeptide of interest fused to a second intracellular tubular protein, under conditions that permit the expression of said first and second intracellular tubular proteins, wherein such expression permits the formation of an intracellular tubular structure, said tubular structure comprising said first and second tubular proteins and displaying a plurality of molecules of said polypeptide of interest.

In one embodiment, the first or second intracellular tubular protein is a VipA polypeptide. Alternatively, the first or second intracellular tubular protein is a VipB polypeptide.

In another embodiment the displayed polypeptide has a conformation substantially similar to the folding pattern of the protein of interest when not displayed in this manner.

In another embodiment, the displayed polypeptide is more immunogenic than the protein of interest when not displayed in this manner.

In another embodiment, the bacterial cell is from the species *Vibrio* or *Pseudomonas*, for example, *Vibrio cholera* or *Psuedomonas aeruginosa*.

In another embodiment, the construct encoding a polypeptide of interest fused to a second intracellular tubular protein is expressed in the bacteria from which the first and second intracellular tubular proteins were derived.

In another embodiment, expression of the construct in the bacteria occurs under conditions in which the secretion of Type VI secretion system substrate proteins is detected. Exemplary Type VI secretion system substrate proteins include e.g., Hcp, VgrG and/or orthologs thereof.

In another embodiment, the polypeptide of interest comprises a viral protein, a bacterial protein, a fungal protein or a tumor protein.

In another embodiment, the method further comprises isolating the tubular structure comprising said first and second tubular proteins and displaying a plurality of molecules of said polypeptide of interest.

In another embodiment, the second intracellular tubular protein is expressed from a vector.

In another embodiment, the plurality of molecules of the polypeptide of interest are displayed as a regular, repetitive structure.

Another aspect described herein relates to a method for making a vaccine comprising combining an isolated tubular structure comprising said first and second tubular proteins and displaying a plurality of molecules of said polypeptide of interest with a pharmaceutically acceptable carrier.

In one embodiment of this aspect, the pharmaceutically acceptable carrier comprises an adjuvant.

In another embodiment, the first or second intracellular tubular protein is a VipA polypeptide. Alternatively, the first or second intracellular tubular protein is a VipB polypeptide.

In another embodiment, the displayed polypeptide has a conformation substantially similar to the folding pattern of the protein of interest when not displayed in this manner.

In another embodiment, the displayed polypeptide is more immunogenic than the protein of interest when not displayed in this manner.

In another embodiment of this aspect, the polypeptide of interest comprises a viral protein, a bacterial protein, a fungal protein or a tumor protein.

In another embodiment, the plurality of molecules of the polypeptide of interest are displayed as a regular, repetitive structure.

Another aspect described herein relates to a fusion protein comprising a polypeptide of interest fused to an intracellular tubular protein.

In some embodiments, the first or second intracellular tubular protein is a VipA polypeptide. In alternative embodiments, the first or second intracellular tubular protein is a VipB polypeptide.

In another embodiment, the displayed polypeptide has a conformation substantially similar to the folding pattern of the protein of interest when not displayed in this manner.

In another embodiment, the displayed polypeptide is more immunogenic than the protein of interest when not displayed in this manner.

In another embodiment, the polypeptide of interest comprises a viral protein, a bacterial protein, a fungal protein or a tumor protein.

In another embodiment, the plurality of molecules of the polypeptide of interest are displayed as a regular, repetitive structure.

Also provided herein in another aspect is an isolated tubular structure comprising: a fusion protein comprising a polypeptide of interest fused to a first intracellular tubular protein, and a second intracellular tubular protein, wherein the tubular structure displays a plurality of molecules of said polypeptide of interest.

In one embodiment, the first or second intracellular tubular protein is a VipA polypeptide. Alternatively, the first or second intracellular tubular protein is a VipB polypeptide.

In another embodiment, the displayed polypeptide has a conformation substantially similar to the folding pattern of the protein of interest when not displayed in this manner.

In another embodiment, the displayed polypeptide is more immunogenic than the protein of interest when not displayed in this manner.

In another embodiment, the first and second intracellular tubular proteins are derived from the genus *Vibrio* or *Pseudomonas*, for example, *Vibrio cholerae* or *Pseudomonas aeruginosa*.

In another embodiment, the plurality of molecules of the polypeptide of interest are displayed as a regular, repetitive structure.

Another aspect provided herein relates to methods for vaccinating a subject, the method comprising: (a) isolating a tubular structure comprising said first and second tubular proteins and displaying a plurality of molecules of said polypeptide of interest from a cultured bacterial cell that expresses a first intracellular tubular protein, and that comprises a construct encoding a polypeptide of interest fused to a second intracellular tubular protein, wherein the bacteria cell is cultured under conditions that permit the expression of said first and second intracellular tubular proteins, wherein such expression permits the formation of an intracellular tubular structure, said tubular structure comprising said first and second tubular proteins and displaying a plurality of molecules of said polypeptide of interest, and (b) administering the isolated tubular structure of step (a) to a subject, thereby vaccinating a subject against the displayed polypeptide of interest.

In one embodiment, the first or second intracellular tubular protein is a VipA polypeptide. In another embodiment, the first or second intracellular tubular protein is a VipB polypeptide.

In another embodiment, the displayed polypeptide has a conformation substantially similar to the folding pattern of the protein of interest when not displayed in this manner.

In another embodiment, the displayed polypeptide is more immunogenic than the protein of interest when not displayed in this manner.

In another embodiment, the polypeptide of interest comprises a viral protein, a bacterial protein, a fungal protein or a tumor protein.

In another embodiment, the bacterial cell is from the species *Vibrio* or *Pseudomonas*, for example, the bacterial cell can be *Vibrio cholera* or *Psuedomonas aeruginosa*.

In another embodiment, the construct encoding a polypeptide of interest fused to a second intracellular tubular protein is expressed in the bacteria from which the first and second intracellular tubular proteins were derived.

In another embodiment, expression of the construct in the bacteria occurs under conditions in which the secretion of Type VI secretion system substrate proteins is detected (e.g., Hcp, VgrG and/or orthologs thereof).

In another embodiment, the method further comprises isolating the tubular structure comprising said first and second tubular proteins and displaying a plurality of molecules of said polypeptide of interest.

In another embodiment, the second intracellular tubular protein is expressed from a vector.

In another embodiment, the plurality of molecules of the polypeptide of interest are displayed as a regular, repetitive structure.

Also provided herein in another aspect is a kit for displaying a polypeptide of interest, the kit comprising: a vector encoding a first intracellular tubular protein of interest, the vector comprising a multiple cloning site for cloning a polypeptide of interest such that upon expression in a cell, a fusion protein comprising the first intracellular tubular protein of interest and the polypeptide of interest is expressed, and instructions therefor.

In one embodiment, the kit further comprises a bacterial cell expressing a second intracellular tubular protein of interest.

In another embodiment, the kit further comprises an additional vector encoding a second intracellular tubular protein of interest.

DETAILED DESCRIPTION

Figure 1A:
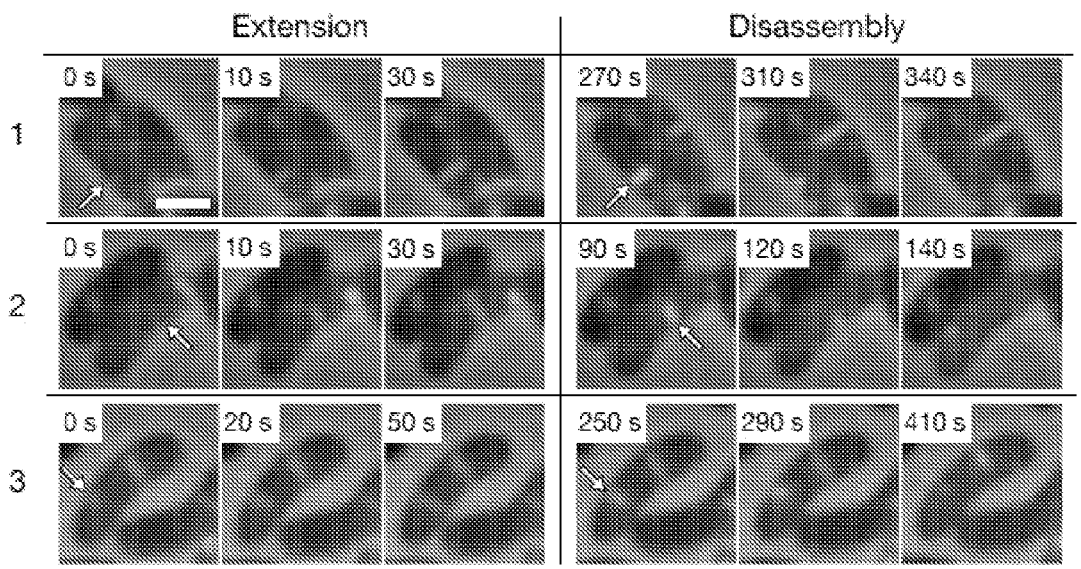
FIGS. 1A-1C Fluorescence light microscopy of VipA-sfGFP. 1A, Individual 3 µm×3 µm frames from a time-lapse imaging with a frame rate of 10 s per frame show three frames of extension of VipA-sfGFP structure in ΔVipA background from one side of the cell to another (arrows) followed by a contraction event and apparent disassembly (shown on three frames) of the contracted VipA-sfGFP structure (arrows). Scale bar on the first frame represents 1 µm. 1B, Kymogram illustrating rapid change in the length of the VipA-sfGFP structure. Projection of signal intensity in time at a rate of 200 frames per second along the axis of the maximal intensity on an extended structure (30 frame average shown on 1C left) showing a contraction in length and increase in maximal intensity of the contracted structure (30 frame average shown on 1C right). Arrows indicate contracting VipA-sfGFP structure and mark the start and end of a line for generating the kymogram. Scale bar shown on 1C left represents 1 µm. Gaussian blur filter (sigma radius=1) was applied to individual frames before generating the kymogram.

The methods and compositions described herein are based, in part, on the discovery that a polypeptide of interest fused to an intracellular tubular protein (e.g., a VipA polypeptide) does not interfere with the ability of the VipA polypeptide to form a tubular structure with another intracellular tubular protein (e.g., a VipB polypeptide). In addition, the Examples described herein indicate that the polypeptide of interest (exemplified herein by a fluorescent moiety, but not limited thereto) can be displayed on the tubular structure in a conformation similar to the conformation observed when the polypeptide of interest is not fused to an intracellular tubular protein or displayed as described above. For example, the studies described herein indicate that when the polypeptide of interest is mCherry or sfGFP, fluorescence can be detected in the cells expressing the fusion protein, which indicates that the folding of mCherry and sfGFP is not adversely affected by fusion to the intracellular tubular protein or the formation of intracellular tubular structures (e.g., T6SS structures).

Thus, provided herein are methods and compositions for displaying a polypeptide on a tubular structure and uses of such displayed polypeptides in the production of antibodies or vaccines.

Definitions

As used herein, the phrase "displaying a polypeptide" means that the protein of interest is "tethered" or fused to the external surface of the tubular structure and is thus displayed or presented to the environment surrounding the tubular structure. Such an arrangement permits access of immune system components to the protein of interest when the tubular structure with the displayed polypeptide is used as a vaccine or to generate antibodies. Thus, in some embodiments, the displayed polypeptide is an antigen. In addition, a plurality of displayed polypeptides are arranged in space such that individual molecules of the protein of interest occur at regularly spaced intervals on the surface of the tubular protein. The proximity of the displayed polypeptides on the tubular structures permits electrostatic forces and other intramolecular interactions to occur among the displayed polypeptides, which can interact with one another in space to form polymeric complexes (e.g., dimers, trimers, tetramers, pentamers, etc.). The interactions among the plurality of displayed polypeptides depends upon the physical interactions between molecules of the protein of interest as well as the conditions under which the tubular structures are exposed.

The term "vaccine" is used herein to define a composition used to elicit an immune response against an antigen within the composition in order to protect or treat an organism against disease.

As used herein, the term "antigen" refers to any substance that prompts an immune response directed against the substance. In some embodiments, an antigen is a peptide, a polypeptide or a displayed polypeptide.

As used herein, the term "fused" means that at least one protein, peptide, or polypeptide is physically associated with a second protein or peptide, such as linkage as a fusion protein.

As used herein, the term "fusion polypeptide" or "fusion protein" means a protein created by joining two or more polypeptide sequences together. The fusion polypeptides encompassed in the methods and compositions described herein include translation products of a chimeric gene construct that joins the DNA sequences encoding one or more antigens, or fragments or mutants thereof, with the DNA sequence encoding an intracellular tubular protein to form a single open-reading frame. In other words, a "fusion polypeptide" or "fusion protein" is a recombinant protein of two or more proteins which are joined by a peptide bond.

As used herein, the term "tubular structure" should be understood as any elongated structure having a proximal end, a distal end and a continuously hollow central lumen extending from the proximal end to the distal end. The proximal and/or distal ends of the tubular structure can be either open or closed. The tubular structure is often hollow; however filled tubular structures are also contemplated herein.

As used herein, the phrase "formation of an intracellular tubular structure" refers to the assembly of two or more intracellular tubular proteins into a 3-dimensional intracellular tubular structure.

As used herein, the term "plurality of molecules" refers to at least two molecules (e.g., two copies) of a polypeptide of interest displayed on the surface of a tubular structure, for example, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 125, at least 150, at least 175, at least 200, at least 300, at least 400, at least 500, at least 600, at least 700, at least 800, at least 900, at least 1000, at least 1500, at least 2000, at least 5000, at least $10^4$, at least $10^5$, or more molecules of the polypeptide of interest are displayed.

The terms "polypeptide" and "protein" are used interchangeably to refer to a polymer of amino acid residues linked by peptide bonds, and for the purposes of the methods and compositions described herein, have a minimum length of at least 25 amino acids. The terms "polypeptide" and "protein" can encompass a multimeric protein, e.g., a protein containing more than one domain or subunit. The term "peptide" as used herein refers to a sequence of peptide bond-linked amino acids containing less than 25 amino acids, e.g., between about 4 amino acids and 24 amino acids in length. Proteins and peptides can be composed of linearly arranged amino acids linked by peptide bonds, whether produced biologically, recombinantly, or synthetically and whether composed of naturally occurring or non-naturally occurring amino acids. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person skilled in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

As used herein, the term "VipA polypeptide" refers to an intracellular tubular protein that forms an intracellular tubular structure a VipB polypeptide. VipA polypeptides are involved in the Type VI secretion system and can be derived from bacterial species including, but not limited to, *Vibrio, Escherichia, Pseudomonas, Agrobacterium* and *Rhizobium* (e.g, *Vibrio cholera, Escherichia coli, Pseudomonas aeruginosa, Agrobacterium tumefaciens*, and *Rhizobium leguminosarum*, among others (see e.g., Das and Chaudhuri, *In Silico Biol* 3:287-300 (2003)). The term "VipA polypeptide" further encompasses natural orthologs, synthetic orthologues, and derivatives thereof. In one embodiment, the VipA protein is (KEGG ref. no. VCA0107; GenBank Accession No. NP_232508) derived from *Vibrio cholerae* or an ortholog thereof. Amino acid and nucleotide sequences for VipA derived from *Vibrio cholerae* are provided herein.

As used herein, the term "VipB polypeptide" refers to an intracellular tubular protein that forms an intracellular tubular structure a VipA polypeptide. VipB polypeptides are involved in the Type VI secretion system and can be derived from bacterial species including, but not limited to, *Vibrio, Escherichia, Pseudomonas, Agrobacterium* and *Rhizobium* (e.g, *Vibrio cholera, Escherichia coli, Pseudomonas aeruginosa, Agrobacterium tumefaciens*, and *Rhizobium leguminosarum*, among others (see e.g., Das and Chaudhuri, *In Silico Biol* 3:287-300 (2003)). The term "VipB polypeptide" further encompasses natural orthologs, synthetic orthologues, and derivatives thereof. In one embodiment, the VipB polypeptide refers to a VipB protein (KEGG ref. no. VCA0108; GenBank Accession No. NP_232509) derived from *Vibrio cholerae* or an ortholog thereof. Amino acid and nucleotide sequences for VipB derived from *Vibrio cholerae* are provided herein.

The term "ortholog" has its usual meaning in the art. The term generally refers to genes in different species that evolved from a common ancestral gene by speciation. Normally, orthologs retain the same function in the course of evolution. As used herein, the term "ortholog" refers to the protein products of the genes as well.

As used herein, the term "more immunogenic" refers to the increased ability of a displayed polypeptide to invoke an immune response compared to the protein of interest that is not displayed as described herein. In some embodiments, the ability of the displayed polypeptide to invoke an immune response can be determined by measuring the amount of antibody production or titer in a cell culture or animal model and comparing that to the amount of antibody production or antibody titer in response to the protein of interest using the same model. At a minimum, a displayed polypeptide is more immunogenic if the antibody titer is at least 10% higher in such an assay. In some embodiments, the immunogenicity of the displayed polypeptide is determined by measuring the activation of immune effector cells. Methods and assays for determining the immunogenicity of the displayed polypeptide are described herein in the section marked "Measuring Immunogenicity." Typically, a displayed polypeptide has an increased immunogenicity of at least 10% compared to the measured indicator of immunogenicity produced by the protein of interest; preferably the displayed polypeptide produces an increase in immunogenicity of at least 20%, at least 30%, at least 40%, at least 50%, at least 60%, at least 70%, at least 80%, at least 90%, at least 95%, at least 98%, at least 99%, at least 1-fold, at least 2-fold, at least 5-fold, at least 10-fold, at least 50-fold, at least 100-fold, at least 500-fold, at least 1000-fold (or more) higher than the immunogenicity observed in the same model in response to the protein of interest that is not displayed using the methods described herein. Without wishing to be bound by theory, it is postulated that polypeptides existing in a higher order structure (e.g., dimer, trimer, tetramer, pentamer, hexamer, heptamer, octamer, nonamer, decamer, or another multimeric or regularly repeating structure or complex) are more immunogenic (e.g., antigenic) than a monomer of the protein of interest. Methods for displaying a polypeptide as described herein allows the polypeptide molecules to interact with one another, thereby forming polymeric or multimeric complexes that are more immunogenic than if the protein of interest was administered in a monomeric form.

The term "adjuvant" as used herein refers to any agent or entity which increases the antigenic response or immune response by a cell or organism to a target antigen. Examples of adjuvants include, but are not limited to mineral gels such as aluminum hydroxide or aluminum phosphate; surface active substances such as lysolecithin, pluronic polyols, polyanions; other peptides; oil emulsions; and potentially useful human adjuvants such as BCG and *Corynebacterium parvum*, QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, Albumin (Alum), CpG ODN, Betafectin, and MF59. In one embodiment, the adjuvant is not Freund's adjuvant (particularly for immunization of human subjects).

The term "subject" as used herein refers to any animal in which it is useful to elicit an immune response. The subject can be a mammal, for example a human, or can be a wild, domestic, commercial or companion animal. While in one embodiment of the invention it is contemplated that the immunogenic compositions as disclosed herein can also be suitable for the therapeutic and/or preventative treatment in humans, it is also applicable to all vertebrates, e.g., mammals, such as non-human primates, (particularly higher primates), sheep, dog, rodent (e.g., mouse or rat), guinea pig, goat, pig, cat, rabbits, cows, and non-mammals such as chickens, amphibians, reptiles etc. In one embodiment, the subject is human. In some embodiments, the subject is an experimental animal or animal substitute as a disease model.

As used herein, the term "pathogen" refers to an organism or molecule that causes a disease or disorder in a subject. For example, pathogens include, but are not limited to, viruses, fungi, bacteria, parasites and other infectious organisms or molecules therefrom, as well as taxonomically related macroscopic organisms within the categories algae, fungi, yeast and protozoa or the like.

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like.

The term "substantially similar," when used in reference to a displayed polypeptide, means that the displayed polypeptide comprises a conformational folding pattern that is similar to that of the protein of interest, for example, in its native conformational folding pattern. As one measure of substantial similarity, an antibody that recognizes the native protein would generally be expected to recognize a displayed polypeptide if that polypeptide is similarly folded. In one embodiment, the term "substantially similar" indicates that the displayed polypeptide is functional. The term "functional" when used in conjunction with a displayed polypeptide, a derivative, or a variant refers to a protein molecule which possesses a biological activity that is substantially similar to a biological activity of the entity or molecule of which it is a derivative or variant (e.g., an un-displayed polypeptide). By "substantially similar" in the context of biological activity is meant that the biological activity, e.g., immunogenicity, fluorescence, enzymatic activity etc. of the subject polypeptides is at least 50% as active as a reference, e.g., a corresponding wild-type polypeptide, and preferably at least 60% as active, 70% as active, 80% as active, 90% as active, 95% as active, 100% as active or even higher (i.e., the variant or derivative has greater activity than the wild-type), e.g., 110% as active, 120% as active, or more.

The term "vectors" refers to a nucleic acid molecule capable of transporting or mediating expression of a heterologous nucleic acid to which it has been linked to a host cell; a plasmid is one species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, useful expression vectors are often in the form of plasmids, circular double stranded DNA molecules which, in their vector form are not bound to the chromosome, and typically comprise entities for stable or transient expression of the encoded DNA. Other expression vectors that can be used in the methods as disclosed herein include, but are not limited to episomes, bacterial artificial chromosomes, yeast artificial chromosomes, bacteriophages or viral vectors; such vectors can integrate into the host's genome or replicate autonomously in the particular cell. A vector can be a DNA or RNA vector. Other forms of expression vectors known by those skilled in the art which serve the equivalent functions can also be used, for example self-replicating extrachromosomal vectors or vectors which integrate into a host genome. Preferred vectors are those capable of autonomous replication and/or expression of nucleic acids to which they are linked.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Described herein are methods and compositions for the preparation of antigens or proteins of interest, e.g., for vaccines. The compositions and methods relate to the expression of an antigen as a fusion protein with a bacterial polypeptide that assembles, with another bacterial polypeptide, into a tubular structure that displays the fused antigen or protein of interest on its surface. Without wishing to be bound by theory, it is believed that the display on the surface of the tubular structure can increase immunogenicity of the displayed polypeptide at least in part because the fused protein of interest can be displayed in a regular, repetitive manner on the surface. The following describes the methods, compositions and considerations necessary for the practice of this technology.

Tubular Proteins

While any bacterial protein that assembles into a tubular structure and maintains the ability to do so when fused to a protein of interest can be used for the methods described herein, the following describes preferred tubular proteins for this purpose.

In one embodiment, the use of VipA and VipB as the intracellular tubular proteins is specifically contemplated.

VipA and VipB are proteins involved in Type VI secretion systems (T6SS) in prokaryotes and play a role in the virulence of *Vibrio cholerae*. VipA/VipB interact to form a tubular structure, also referred to as a 'sheath.' A perpendicular view of a purified tubular structure comprising VipA/VipB shows a cog-wheel like structure having 12 paddles (FIG. 3E). As described herein in detail in the Examples section, the VipA/VipB structures are analogous to in structure to a bacteriophage tail.

The amino acid and nucleotide sequences for VipA and VipB are shown below.

```
VipA: Amino acid sequence
                                        (SEQ ID NO: 1)
MSKEGSVAPKERINIKYIPATGDAQAEVELPLKTLVVGDFKGHAEQTPLE

ERATVTVDKNNFEAVMRESELKITATVKNKLTDDENAELPVELNFKSLAD

FAPDAVASQVPELKKLIELREALVALKGPLGNIPAFRERLQSLLNSEESR

EKLLAELNLLSGQEEPQA

VipA: nucleotide sequence
                                        (SEQ ID NO: 2)
atgtctaaagaaggaagtgtagctcccaaagagcggattaatatcaagta tattccggcgacgggggatgcacaggctgaggttgagctaccactcaaaa ccctagttgtaggtgatttcaaagggcatgcggagcaaaccccattggaa gagcgtgcaacagtcacggtagataagaacaactttgaagccgtaatgcg cgagagcgagctgaaaatcaccgccacggtgaaaaacaagctgactgatg
```

-continued
```
atgagaatgccgagcttcctgttgaactcaatttcaaatccttagccgac ttcgctcctgatgcggtggcatcacaagttccagaactgaaaaaattgat tgagttgcgtgaagcgttagttgcccttaaagggccgctaggcaacattc ccgcatttcgtgagcgtttacagtcattactcaactcagaagagtcgaga gaaaagctgttggcagaactgaatctgctcagtggtcaagaagagccaca agcgtaa
```

VipB: Amino acid sequence
(SEQ ID NO: 3)
```
MMSTTEKVLERPQLAQGSLLDEIMAQTRIAPSEEGYDIAKKGVAAFIENL

MGSQHSAEPVNKSLVDQMLVELDKKISAQMDEILHNSQFQAMESAWRGLK

LFVDRTDFRENNKVEILHVTKDELLEDFEFAPETAQSGLYKHVYSAGYGQ

FGGEPVGAIIGNYAFTPSTPDMKLLQYMGALGAMAHAPFISSVGPEFFGI

DSFEELPNIKDLKSTFESPKYTKWRSLRESEDARYLGLTAPRFLLRVPYD

PIENPVKSFNYAENVSASHEHYLWGNTAFAFATRLTDSFAKYRWCPNIIG

PQSGGAVEDLPVHVFESMGALQSKIPTEVLITDRKEFELAEEGFIALTMR

KGSDNAAFFSANSIQKPKVFPNTKEGKEAETNYKLGTQLPYMMIINRLAH

YVKVLQREQIGAWKERQDLERELNSWIKQYVADQENPPADVRSRRPLRAA

RIEVMDVEGNPGWYQVSLSVRPHFKYMGANFELSLVGRLDQA
```

VipB: Nucleotide sequence
(SEQ ID NO: 4)
```
atgatgtctacgactgaaaaggtattggaaaggccacagcttgctcaagg cagccttcttgatgaaattatggcgcaaacccgtatcgcaccaagcgaag agggttacgacatcgcgaaaaaggtgttgcagcgtttatcgaaaatcttt atgggttcacaacactctgctgagcctgtcaacaaatctctggttgacca aatgttggttgaactggataaaaaaatcagtgcacagatggatgaaatcc tgcacaactcacaattccaagcgatggaatcggcgtggcgcggtttgaag ctgttcgtggatcgcactgattttcgtgaaaataacaaagtcgaaatcct tcacgtaaccaaagatgaactgctggaagatttcgagtttgctccagaaa cggctcagtccggtctttacaagcacgtttattctgccggttatggtcaa tttggtggcgaacctgttggcgcgatcattggtaactatgcgtttacccc ttcaacgccagatatgaagctgctgcaatacatgggcgcactgggtgcca tggcgcatgctcctttcatttcaagcgtaggtcctgaattctttggtatc gactccttcgaagaactgcctaacattaaagatctcaagtcgacatttga aagcccgaaatacaccaaatggcgttcactgcgtgaatcggaagatgctc gctatcttggtttgactgcgcctcgtttcctgctgcgtgttccttacgat ccaatcgaaaatccagtgaagtcgttcaattatgcggaaaacgtcagtgc ttcgcacgagcactacctgtggggtaacacggcatttgccttcgcaactc gtttgacggatagctttgctaaatatcgctggtgtccaaacattatcggt ccacaaagtggtggtgcagttgaagatctgccggtgcatgtctttgaatc tatgggtgcattgcaaagcaagatcccaaccgaagtcctgatcacggacc gtaaagaatttgaactggcggaagaaggttttattgctcttactatgcgt aaaggcagtgataacgcggcgttcttctctgcaaactccattcaaaaacc taaggttttcccaaataccaaagaaggcaaagaagcggaaaccaactaca
```

-continued
```
agttgggtacccagttgccgtacatgatgatcatcaaccgtttggcgcac tatgtgaaagttctgcaacgtgagcagatcggtgcttggaaagagcgtca agatcttgagcgtgaactgaactcatggatcaaacaatacgttgctgatc aagagaacccacctgcagacgtacgtagccgtcgtccacttcgtgctgcg cgcattgaagtgatggatgtggaaggcaatccaggttggtatcaggtgtc gctctcggttcgtcctcactttaagtacatgggtgcgaactttgagttgt cattagttggacgtcttgatcaagcctga
```

In addition, orthologs of VipA and VipB found in other prokaryotes can be used with the methods and compositions described herein. For example, orthologs of VipA and VipB can be derived from *Escherichia coli, Pseudomonas aeruginosa, Agrobacterium tumefaciens,* and *Rhizobium leguminosarum,* among others (see e.g., Das and Chaudhuri, *In Silico Biol* 3:287-300 (2003)).

In some embodiments of the aspects described herein, the first and/or second intracellular tubular proteins comprise an amino acid sequence that is at least about 50%, at least about 55%, at least about 60%, at least about 65%, at least about 70%, at least about 75%, at least about 80%, at least about 85%, at least about 90%, at least about 95%, at least about 99%, or more homologous to an amino acid sequence of SEQ ID NOs: 1 and 3. In other embodiments of the aspects described herein, the intracellular tubular protein has an amino acid sequence that is encoded by a nucleotide sequence that is at least about 50%, at least about 60%, at least about 70%, at least about 80%, at least about 90%, at least about 95%, or more, homologous to a nucleotide sequence of SEQ ID NOs: 2 and 4.

In some embodiments, the intracellular tubular proteins comprise one or more conservative amino acid substitutions. It is also contemplated herein that the protein of interest and/or the displayed polypeptide also comprise one or more conservative amino acid substitutions. As well-known in the art, a "conservative substitution" of an amino acid or a "conservative substitution variant" of a polypeptide refers to an amino acid substitution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or histidine. "Negatively charged residues" refer to aspartic acid or glutamic acid. Residues having "bulky side chains" refer to phenylalanine, tryptophan or tyrosine. To avoid doubt as to nomenclature, the term "D144N" or similar terms specifying other specific amino acid substitutions means that the Asp (D) at position 144 is substituted with Asn (N). A "conservative substitution variant" of D144N would substitute a conservative amino acid variant of Asn (N) that is not D.

The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the table below. A conservative substitution mutant or variant will 1) have only conservative amino acid substitutions relative to the parent sequence, 2)

will have at least 90% sequence identity with respect to the parent sequence, preferably at least 95% identity, 96% identity, 97% identity, 98% identity or 99% or greater identity; and 3) will retain biological activity of the protein of interest.

| CONSERVATIVE AMINO ACID REPLACEMENTS | | |
| --- | --- | --- |
| For Amino Acid | Code | Replace With |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, He, D-Ile, Met, D-Met, AdaA, AdaG |

In other embodiments, derivatives of an intracellular tubular protein or the protein of interest with amino acid substitutions which are less conservative may also result in desired derivatives, e.g., by causing changes in charge, conformation and other biological properties. Such substitutions would include, for example, substitution of a hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics. The polypeptides and proteins as described herein may also be modified by various changes such as insertions, deletions and substitutions, either conservative or nonconservative where such changes might provide for certain advantages in their use.

Fusion Proteins

In general, any polypeptide antigen can be displayed on the surface of an intracellular tubular structure using the methods described herein, provided that the polypeptide does not interfere with the assembly of the first and second intracellular tubular proteins into a tubular structure. For example, the polypeptide to be displayed is not so large that formation of the tubular structure is impeded. One of skill in the art will readily recognize when a polypeptide to be displayed interferes with the formation of a tubular structure as described herein. The methods and compositions described herein are particularly useful in the fields of antibody production and vaccine production. Thus, in general, a polypeptide to be displayed using the methods described herein is an antigenic polypeptide for use in generating antibodies or vaccines.

A protein of interest is first selected and the nucleotide sequence encoding the protein of interest is cloned into an expression vector together with a nucleotide sequence encoding a second intracellular tubular protein. The construct is generated such that the nucleotide sequence encoding the protein of interest and the first intracellular tubular protein comprise the same open reading frame, thereby permitting expression of a fusion protein in a bacterial cell.

As exemplified herein, the fusion protein comprises a polypeptide to be displayed fused to the C-terminus of an intracellular tubular protein (e.g., VipA). However, fusion proteins comprising a protein of interest fused to the N-terminus of an intracellular tubular protein are also contemplated herein. Methods for producing fusion proteins are well known to those of skill in the art, and as such are not described in detail herein.

The fusion proteins as used with the methods described herein will preferably not interfere with the proper conformational folding of the protein of interest or the tubular protein. In addition, the fusion protein does not impair the ability of the second intracellular tubular protein to interact with a first intracellular tubular protein and the subsequent formation of an intracellular tubular structure.

Displaying a Polypeptide on a Tubular Structure

Methods for displaying a polypeptide on a tubular structure involve the use of standard molecular and cell biology techniques known to those of skill in the art. Briefly, a vector encoding a fusion protein comprising a protein of interest and a second intracellular tubular protein is introduced to a bacterial cell culture under conditions that permit expression of the fusion protein. The bacteria are maintained in culture to permit the interaction of the first intracellular tubular protein and the second intracellular tubular protein as described herein, such that an intracellular tubular structure displaying a polypeptide is assembled.

The cells can be lysed and standard isolation procedures can be applied to isolate the tubular structure displaying the polypeptide from the remaining contents of the culture (e.g., media, cell lysate etc.). In some embodiments, the fusion protein can further comprise a tag sequence to aid in isolation of the tubular structure displaying the polypeptide. Exemplary tag sequences include, but are not limited to, a His-tag, a myc-tag, a FLAG-tag, a T7-tag, an HA (hemagglutinin)-tag, an S-tag, a GST-tag, and a GFP-tag.

Regular, Repetitive Structures

The first and second tubular polypeptides described herein assemble into a tubular structure that displays a fused polypeptide of interest on its surface in a regular, repetitive pattern or structure.

In one sense, a "regular, repetitive structure" as used herein is analogous to a crystal structure, in which identical units comprising the crystal are arranged in space in a 3-dimensional pattern that makes up the crystal. Thus, a regular repetitive structure as the term is used herein comprises identical protein subunits of the protein of interest arranged in a pattern such that the distances between the adjacent subunits are substantially the same for any two adjacent subunits.

That is, the assembly of the first and second polypeptides generates a pattern in which the displayed polypeptide is arranged in space such that individual molecules of the protein of interest occur at regularly spaced intervals on the surface of the assembly. By regularly spaced intervals is meant that the distance between two adjacent molecules (or, alternatively, between higher order complexes of the protein of interest e.g., a trimer arrangement) is substantially the same for any two adjacent molecules of interest.

Bacterial Expression Systems

The tubular structure displaying a polypeptide can be expressed in essentially any bacterial system, including bacteria in which the expression constructs are introduced into the bacteria using phage or other appropriate methods, provided that the bacterial expression system permits the assembly of the tubular structure from the expressed fusion protein and a second intracellular tubular protein. Bacterial expression systems are well known in the art, and include, for example, *Bacillus subtilis, Escherichia coli, Streptococcus cremoris, Streptococcus lividans, Corynebacterium glutamicum*, and *Salmonella typhimurium*, among others. In some embodiments, it is preferred that the fusion protein is expressed in a bacterial strain from which the first and second intracellular tubular proteins are derived. In such embodiments, the bacterial culture is grown under conditions in which the Type VI secretion system (T6SS) is functionally expressed (e.g., as determined by measuring secretion of one or more substrate proteins including Hcp and VgrG or orthologs thereof). Thus, in some embodiments, the tubular structures displaying a polypeptide are expressed in bacteria from the following species: *Vibrio, Pseudomonas, Escherichia, Agrobacterium* or *Rhizobium*, among others. Some exemplary strains of such bacteria include, for example, *Vibrio cholerae, Escherichia coli, Pseudomonas aeruginosa, Agrobacterium tumefaciens*, and *Rhizobium leguminosarum*.

A variety of expression vectors may be utilized to express the tubular structures as described herein. The expression vectors are constructed to be compatible with the host cell type. Expression vectors may comprise self-replicating extrachromosomal vectors or vectors which integrate into a host genome. Expression vectors typically comprise the fusion construct, control or regulatory sequences, selectable markers, and/or additional elements. Preferred bacterial expression vectors include but are not limited to pET, pBAD, bluescript, pUC, pQE, pGEX, pMAL, and the like. Generally, expression vectors include transcriptional and translational regulatory nucleic acid sequences which are operably linked to the nucleic acid sequence encoding the fusion protein. The transcriptional and translational regulatory nucleic acid sequences will generally be appropriate to the host cell used to express the fusion protein and tubular structure, as will be appreciated by those in the art. For example, transcriptional and translational regulatory sequences from *E. coli* are preferably used to express the tubular structure in *E. coli*.

Transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences comprise a promoter and transcriptional and translational start and stop sequences.

A suitable promoter is any nucleic acid sequence capable of binding RNA polymerase and initiating the downstream (3') transcription of the coding sequence into RNA. Promoter sequences may be constitutive or inducible. The promoters may be naturally occurring promoters, hybrid or synthetic promoters.

A suitable bacterial promoter has a transcription initiation region which is usually placed proximal to the 5' end of the coding sequence. The transcription initiation region typically includes an RNA polymerase binding site and a transcription initiation site. In *E. coli*, the ribosome-binding site is called the Shine-Dalgarno (SD) sequence and includes an initiation codon and a sequence of 3-9 nucleotides in length located 3-11 nucleotides upstream of the initiation codon. Promoter sequences for metabolic pathway enzymes are commonly utilized. Examples include promoter sequences derived from sugar metabolizing enzymes, such as galactose, lactose and maltose, and sequences derived from biosynthetic enzymes such as tryptophan. Promoters from bacteriophage, such as the T7 promoter, may also be used. In addition, synthetic promoters and hybrid promoters are also useful; for example, the tac promoter is a hybrid of the trp and lac promoter sequences.

In addition, in a preferred embodiment, the expression vector contains a selection gene or marker to allow the selection of transformed host cells containing the expression vector. Selection genes are well known in the art and will vary with the host cell used. For example, a bacterial expression vector may include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline.

Displayed Polypeptide Antigens

The immunogenic compositions or displayed polypeptides as disclosed herein can be any antigen which elicits an immune response in a subject. In some embodiments, at least one or more different antigens are displayed by the tubular structure described herein. In some embodiments, at least about 2, or at least about 3, or at least about 5, or at least about 10 different antigens can be associated with the polymer as disclosed herein. In some embodiments, the immunogenic composition comprises a plurality (e.g., at least 2) of molecules (e.g., copies) of a displayed polypeptide(s). In some embodiments, where the immunogenic composition comprises more than one antigen, the antigens can be antigens from the same pathogen or from multiple different pathogens, or alternatively, can be different antigens from the same pathogen, or similar antigens from different serotypes of pathogens.

An antigen for use in the immunogenic compositions and methods described herein can be any antigen, including, but not limited to pathogenic peptides, toxins, toxoids, subunits thereof, or combinations thereof (e.g., cholera toxin, tetanus toxoid, among others).

In some embodiments, an antigen (e.g., a displayed polypeptide) can be any antigen associated with an infectious disease, or cancer or immune disease. In some embodiments, an antigen can be an antigen expressed by any of a variety of infectious agents, including virus, bacterium, fungus or parasite.

In some embodiments, an antigen is derived (e.g., obtained) from a pathogenic organism. In some embodiments, the antigen is a cancer or tumor antigen.

In some embodiments, an antigen can be an intact (i.e., an entire or whole) antigen, or a functional fragment of an antigen. In some embodiments, an antigen is a peptide functional fragment of an antigen. By "intact" in this context is meant that the antigen is the full length antigen as that antigen polypeptide occurs in nature. This is in direct contrast to delivery of only a small portion or peptide of the antigen. Delivering an intact antigen to a cell enables or facilitates eliciting an immune response to a full range of epitopes of the intact antigen, rather than just a single or selected few peptide epitopes.

Alternatively, in some embodiments, an intact antigen can be divided into many parts, depending on the size of the initial antigen. Typically, where a whole antigen is a multimeric polypeptide, the whole protein can be divided into sub-units and/or domains where each individual sub-unit or domain of the antigen can be displayed by the tubular structure according to the methods as disclosed herein.

A target antigen for use in the methods and compositions described herein can be expressed by recombinant means, and can optionally include an affinity or epitope tag to facilitate purification (Summers and Smith, 1987; Goeddel, 1990; Ausubel et al., 1996).

It is understood that a variety of buffers and solutions can be admixed with the isolated intracellular tubular structure displaying a polypeptide. One of skill in the art can identify a solution that maintains the displayed polypeptides such that they are more immunogenic (as that term is used herein) than their undisplayed counterparts. These conditions can vary based on the characteristics of the displayed protein in different solutions. In some embodiments, an antigen can be solubilized in water, a solvent such as methanol, or a buffer. Suitable buffers include, but are not limited to, phosphate buffered saline Ca 2+/Mg2+ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous solvent for use the compositions, methods and kits described herein.

Typically when designing a protein vaccine against a pathogen, an extracellular protein or one exposed to the environment on a virus is often the ideal candidate as the antigen component in the vaccine. Antibodies generated against that extracellular protein become the first line of defense against the pathogen during infection. The antibodies bind to the protein on the pathogen to facilitate antibody opsonization and mark the pathogen for ingestion and destruction by a phagocyte such as a macrophage. Antibody opsonization can also kill the pathogen by antibody-dependent cellular cytotoxicity. The antibody triggers a release of lysis products from cells such as monocytes, neutrophils, eosinophils, and natural killer cells.

Methods of vaccination and challenging an immunized animal are known to one skilled in the art, for example as described by LaBarre and Lowy (2001) (J. Virol. Methods 96:107-26) and by Orville J. Golub (1948) (J. Immunol., 59:71-82) which are incorporated hereby reference in their entirety.

In one embodiment of the invention described herein, antigens for use in the compositions as disclosed herein comprise the same amino acid sequence as the wild type protein; that is the sequences are found in naturally occurring viruses and have not been altered by selective growth conditions or molecular biological methods.

Antigens from Pathogenic Organisms

In some embodiments, an antigen derived from a pathogenic organism is an antigen associated with an infectious disease; it can be derived from any of a variety of infectious agents, including virus, bacterium (e.g., a gram positive or gram negative bacterium), fungus or parasite.

In one embodiment, the pathogenic organism is a virus. In such embodiments, the displayed polypeptide can be a protein on the external surface of the virus (e.g., a viral coat protein).

In another embodiment, the pathogenic organism is a bacterium. In such embodiments, the displayed polypeptide can be a bacterial surface protein (e.g., a capsule protein, a trypsin-sensitive protein, M protein, a virulence protein, an invasin protein, a superantigen protein, a fibronectin binding protein, an extracellular lipoprotein, a carbohydrate-protein conjugate, and a polysaccharide protein conjugate, among others).

In some embodiments, the antigen to be displayed on a tubular structure as described herein comprises a protein secreted from a bacterium, fungus or parasite (e.g., an exotoxin).

In another embodiment, the pathogenic organism is a fungus. In such embodiments, the displayed polypeptide can be a surface fungal protein (e.g., a beta-glucan, a glycoprotein, a polysaccharide, a capsule carbohydrate, a virulence protein, an adhesion protein, an aspartic proteinase, and melanin, among others).

In another embodiment, the pathogenic organism is a parasite. Parasite proteins can be derived from any stage of parasite development including pre-erythrocytic, sexual and asexual phases. In such embodiments, the displayed polypeptide can be a surface protein on the parasite (e.g., a sporozoite protein such as circumsporozoite, among others).

In another embodiment, the displayed polypeptide is a synthetic immunogen (see e.g., Guenaga, J et al., *PloS ONE* (2011) 6(1):e1607).

Exemplary Viral Pathogens

Non-limiting examples of pathogens of interest include Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Human T-cell Leukemia virus type-1, Hantavirus, Rubella virus, Rinderpest, Rhinovirus, Echovirus, Papova virus, Echinovirus, Arbovirus, Human Immunodeficiency virus type I or type II and Simian Immunodeficiency virus.

In some embodiments, a target antigen is any antigen associated with a pathogenic state, for example an infectious disease or pathogen, or cancer or an immune disease such as an autoimmune disease. In some embodiments, an antigen can be expressed by any of a variety of infectious agents, including virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

Other viral antigens include, in particular, herpes viruses including herpes simplex viruses, cytomegalovirus, Epstein-Barr virus, and varicella-zoster virus. Other common viral causes of disease in humans and animals may also be targeted, including influenza, adenoviruses, enteroviruses, and hemorrhagic viruses.

In some embodiments, where the antigen is to generate an influenza vaccine, the surface glycoproteins hemagglutinin (HA) and neuraminidase (NA) are generally the antigens of choice. Both nucleoprotein (NP) polypeptide and matrix (M) are internal viral proteins and therefore not usually considered in vaccine design for antibody-based immunity.

In some embodiments, an antigen for use in the immunogenic compositions as disclosed herein can also include those used in biological warfare, such as ricin.

In some embodiments, the displayed polypeptide provides an antigen for the HIV virus including, e.g., env and Gag gene products encoded by HIV. Gag gene products include, but are not limited to, Gag-polymerase (pol) and Gag-protease (prot). Env gene products include, but are not limited to, monomeric gp120 polypeptides, oligomeric gp140 polypeptides (o-gp140) and gp160 polypeptides.

The use of HIV Env polypeptides in immunogenic compositions has been described, (see, U.S. Pat. No. 5,846,546 to Hurwitz et al., issued Dec. 8, 1998, describing immunogenic compositions comprising a mixture of at least four different recombinant virus that each express a different HIV env variant; and U.S. Pat. No. 5,840,313 to Vahlne et al., issued Nov. 24, 1998, describing peptides which correspond to epitopes of the HIV-1 gp120 protein). In addition, U.S. Pat. No. 5,876,731 to Sia et al, issued Mar. 2, 1999 describes candidate vaccines against HIV comprising an amino acid sequence of a T-cell epitope of Gag linked directly to an amino acid sequence of a B-cell epitope of the V3 loop protein of an HTV-1 isolate containing the sequence GPGR (SEQ ID NO: 15). However, these groups did not identify an effective HIV vaccine.

Exemplary Bacterial Pathogens

In one aspect of the invention, an antigen is derived from Staphylococci, Streptococci, *Brucella*, Enterococci species; *Listeria, Bacillus, Corynebacteria, Neisseria meningitidis, Neisseria gonorrheae, Moraxella*, typeable or nontypeable *Haemophilus, Pseudomonas, Salmonella, Shigella, Enterobacter, Citrobacter, Klebsiella, E. coli, Clostridia, Bacteroides, Chlamydiaceae, Mycoplasma, Legionella, Treponemes, Borrelia*, mycobacteria (tuberculous, non-tuberculous, leprae), *Candida* or other yeast or other fungi, *Plasmodium, Amoeba*, herpes viruses, cytomegalovirus, Epstein-barr virus, varicella-zoster virus, influenza, adenoviruses, enteroviruses, or hemorrhagic viruses.

In another aspect of the invention, an antigen is a truncated pneumococcal PsaA protein, pneumococcal serine/threonine protein kinase (StkP), pneumococcal serine/threonine protein kinase repeating unit (StkPR), pneumococcal PcsB protein, *Mycobacterium tuberculosis* mtb protein ESAT-6, *M. tuberculosis* cell wall core antigen, *Chlamydia* CT144, CT242 or CT812 polypeptides or fragments of these, *Chlamydia* DNA gyrase subunit B, *Chlamydia* sulfite synthesis/biphosphate phosphatase, *Chlamydia* cell division protein FtsY, *Chlamydia* methionyl-tRNA synthetase, *Chlamydia* DNA helicase (uvrD), *Chlamydia* ATP synthase subunit I (atpI), or *Chlamydia* metal dependent hydrolase.

In some embodiments, an antigen is from a bacterium, e.g., but not limited to, *M. tuberculosis, mycobacterium*, mycoplasma, *neisseria* and *legionella*. Examples of parasites include, but are not limited to, *rickettsia* and *chlamydia*.

Bacterial pathogens can include, but are non-limited to, anthrax, *campylobacter*, cholera, diphtheria, enterotoxigenic *E. coli*, giardia, gonococcus, *Helicobacter pylori* (Lee and Chen, 1994), *Hemophilus influenza* B, *Hemophilus influenza* non-typable, meningococcus, pertussis, pneumococcus, *salmonella, shigella, Streptococcus* B, group A *Streptococcus*, tetanus, *Vibrio cholerae, Yersinia, Staphylococcus, Pseudomonas* species, *mycobacterium*, mycoplasma, *neisseria, legionella* and *Clostridia* species.

Examples of other intracellular bacterial parasites that can be assayed for infection or exposure using the assays described herein include, but are not limited to, *Rickettsia* and *Chlamydia* species. Additional parasite pathogens include, for example: *Entamoeba histolytica* (Zhang et al., 1995); *Plasmodium* (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991), *Leishmania* (Frankenburg et al., 1996), Toxoplasmosis, and the Helminths.

In one embodiment, the pathogen is *Myocobacterium tuberculosis* (TB), an intracellular bacterial parasite that causes tuberculosis in humans. One example of a TB antigen is TbH9 (also known as Mtb 39A). Other TB antigens include, but are not limited to, DPV (also known as Mtb8.4), 381, Mtb41, Mtb40, Mtb32A, Mtb9.9A, Mtb9.8, Mtb16, Mtb72f, Mtb59f, Mtb88f, Mtb71f, Mtb46f and Mtb31f ("f" indicates that it is a fusion or two or more proteins).

As noted above, an antigen can be derived from a *Chlamydia* species for use in the immunogenic compositions of the present invention. Chlamydiaceae (consisting of *Chlamydiae* and *Chlamydophila*), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present invention include, for example, *C. trachomatis, Chlamydophila pneumoniae, C. muridarum, C. suis, Chlamydophila abortus, Chlamydophila psittaci, Chlamydophila caviae, Chlamydophila felis, Chlamydophila pecorum*, and *C. pneumoniae*. Animal models of chlamydial infection have established that T-cells play a critical role both in the clearance of the initial infection and in protection from re-infection of susceptible hosts. Hence, the immunogenic compositions as disclosed herein can be used to provide particular value by eliciting cellular immune responses against chlamydial infection.

More specifically, Chlamydial antigens useful in the present invention include DNA gyrase subunit B, sulfite synthesis/biphosphate phosphatase, cell division protein FtsY, methionyl-tRNA synthetase, DNA helicase (uvrD); ATP synthase subunit I (atpI) or a metal-dependent hydrolase (U.S. Patent Application Pub. No. 20090028891). Additional *Chlamyidia trachomatis* antigens include CT144 polypeptide, a peptide having amino acid residues 67-86 of CT144, a peptide having amino acid residues 77-96 of CT144, CT242 protein, a peptide having amino acids 109-117 of CT242, a peptide having amino acids 112-120 of CT242 polypeptide, CT812 protein (from the pmpD gene), a peptide having amino acid residues 103-111 of the CT812 protein; and several other antigenic peptides from *C. trachomatis*: NVTQDLTSSTAKLECTQDLI (SEQ ID NO: 5), AKLECTQDLIAQGKLIVTNP (SEQ ID NO: 6), SNLKRMQKI (SEQ ID NO: 7), AALYSTEDL (SEQ ID NO: 8), FQEKDADTL (SEQ ID NO: 9), QSVNELVYV (SEQ ID NO: 10), LEFASCSSL (SEQ ID NO: 11), SQAEGQYRL (SEQ ID NO: 12), GQSVNELVY (SEQ ID NO: 13), and QAVLLLDQI (SEQ ID NO: 14) (as disclosed in WO 2009/020553, which is incorporated herein in its entirety by reference). Additionally, *Chlamydia pneumoniae* antigens including homologues of the foregoing polypeptides (see U.S. Pat. No. 6,919,187 which is incorporated herein in its entirety by reference), can be used an antigens in the immunogenic compositions and methods as disclosed herein.

Exemplary Fungal Antigens

Fungal antigens can be derived from *Candida* species and other yeast; or other fungi (aspergillus, other environmental fungi). Regarding other parasites, malaria as well as worms and amoebae may provide the antigenic antigen for use in the immunogenic compositions and methods as disclosed herein.

Additionally, the present invention also provides immunogenic compositions comprising antigens which raise an immune response against cancer. In these conjugates, an antigen is an antigen expressed by a cancer or tumor, or derived from a tumor. In some embodiments, such antigens are referred to herein as a "cancer antigen" and are typically a protein expressed predominantly on the cancer cells, such that the conjugate elicits both potent humoral and potent cellular immunity to this protein. A large number of cancer-associated antigens have been identified, several of which are now being used to make experimental cancer treatment vaccines and are thus suitable for use in the present embodiments. Antigens associated with more than one type of cancer include Carcinoembryonic antigen (CEA); Cancer/testis antigens, such as NY-ESO-1; Mucin-1 (MUC1) such as Sialyl Tn (STn); Gangliosides, such as GM3 and GD2; p53 protein; and HER2/neu protein (also known as ERBB2). Antigens unique to a specific type of cancer include a mutant form of the epidermal growth factor receptor, called EGFRvIII; Melanocyte/melanoma differentiation antigens, such as tyrosinase, MART1, gp100, the lineage related cancer-testis group (MAGE) and tyrosinase-related antigens; Prostate-specific antigen; Leukaemia-associated antigens (LAAs), such as the fusion protein BCR-ABL, Wilms' tumour protein and proteinase 3; and Idiotype (Id) antibodies. See, e.g., Mitchell, 3 Curr. Opin. Investig. Drugs 150-58 (2002); Dao & Scheinberg, 21 Best Pract. Res. Clin. Haematol. 391-404 (2008).

Exemplary Cancer and/or Tumor Antigens

Another approach in generating an immune response against cancer employs antigens from microbes that cause or contribute to the development of cancer. These vaccines have been used against cancers including hepatocellular carcinoma (hepatitis B virus, hepatitis C virus, Opisthorchis viverrin), lymphoma and nasoparyngeal carcinoma (Epstei-Barr virus), colorectal cancer, stomach cancer (*Helicobacter pylori*), bladder cancer (*Schisosoma hematobium*), T-cell leukemia (human T-cell lymphtropic virus), cervical cancer (human papillomavirus), and others. To date, there have been clinical trials for vaccines targeting Bladder Cancer, Brain Tumors, Breast Cancer, Cervical Cancer, Kidney Cancer, Melanoma, Multiple Myeloma, Leukemia, Lung Cancer, Pancreatic Cancer, Prostate Cancer, and Solid Tumors. See Pardoll et al., Abeloff's Clin. Oncol. (4th ed., Churchill Livingstone, Philadelphia 2008); Sioud, 360 Methods Mol. Bio. 277-318 (2007); Pazdur et al., 30(3) J. Infusion Nursing 30(3):173-78 (2007); Parmiani et al., 178 J. Immunol. 1975-79 (2007); Lollini et al., 24 Trends Immunol. 62-66 (2003); Schlom et al., 13 Clin. Cancer Res. 3776-82 (2007); Bancherau et al., 392 Nature 245-52 (1998); Finn, 358 New Engl. J. Med. 2704-15 (2008); Curigliano et al., 7 Exp. Rev. Anticancer Ther. 1225-41 (2007). Thus, the present embodiments encompass both preventive/prophylactic cancer vaccines and treatment/therapeutic cancer vaccines.

Contemplated proliferative diseases and cancers include AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, astrocytoma, ataxia-telangiectasia, basal cell carcinoma (skin), bladder cancer, bone cancers, bowel cancer, brain and CNS tumors, breast cancer, carcinoid tumors, cervical cancer, childhood brain tumours, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofibrosarcoma-protuberans, desmoplastic-small-round-cell-tumour, ductal carcinoma, endocrine cancers, endometrial cancer, ependymoma, esophageal cancer, Ewing's sarcoma, extra-hepatic bile duct cancer, eye cancer, including, e.g., eye melanoma and retinoblastoma, fallopian tube cancer, fanconi anemia, fibrosarcoma, gall bladder cancer, gastric cancer, gastrointestinal cancers, gastrointestinal-carcinoid-tumour, genitourinary cancers, germ cell tumors, gestational-trophoblastic disease, glioma, gynecological cancers, hematological malignancies, hairy cell leukemia, head and neck cancer, hepatocellular cancer, hereditary breast cancer, Hodgkin's disease, human papillomavirus-related cervical cancer, hydatidiform mole, hypopharynx cancer, islet cell cancer, Kaposi's sarcoma, kidney cancer, laryngeal cancer, leiomyosarcoma, leukemia, Li-Fraumeni syndrome, lip cancer, liposarcoma, lung cancer, lymphedema, lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, renal cell carcinoma, retinoblastoma, rhabdomyosarcoma, Rothmund-Thomson syndrome, salivary gland cancer, sarcoma, Schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer (renal-pelvis/ureter), trophoblastic cancer, urethral cancer, urinary system cancer, uterine sarcoma, uterus cancer, vaginal cancer, vulva cancer, Waldenstrom's-macroglobulinemia, and Wilms' tumor.

Exemplary Autoimmunity Antigens

In some embodiments, an antigen for use in the immunogic compositions as disclosed herein can include antigens of autoimmune diseases, e.g., they can be self antigens. Autoimmune diseases contemplated for diagnosis according to the assays described herein include, but are not limited to alopecia greata, ankylosing spondylitis, antiphospholipid syndrome, Addison's disease, aplastic anemia, multiple sclerosis, autoimmune disease of the adrenal gland, autoimmune hemolytic anemia, autoimmune hepatitis, autoimmune oophoritis and orchitis, Behcet's Disease, bullous pemphigoid, cardiomyopathy, celiac sprue-dermatitis, chronic fatigue syndrome, chronic inflammatory demyelinating syndrome (CFIDS), chronic inflammatory polyneuropathy, Churg-Strauss syndrome, cicatricial pemphigoid, CREST Syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), Lichen Planus, lupus, Meniere's Disease, mixed connective tissue disease, myasthenia gravis, myocarditis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, uveitis, vasculitis and vitiligo. It is generally important to assess the potential or actual CMI responsiveness in subjects having, or suspected of having or being susceptible to an autoimmune disease.

In some embodiments, an antigen for use in the immunogenic compositions as disclosed herein can be an antigen which is associated with an inflammatory disease and/or condition. Examples of inflammatory disease conditions where antigens may be useful include but are not limited to acne, angina, arthritis, aspiration pneumonia, empyema, gastroenteritis, necrotizing enterocolitis, pelvic inflammatory disease, pharyngitis, pleurisy, chronic inflammatory demyelinating polyneuropathy, chronic inflammatory demyelinating polyradiculoneuropathy, and chronic inflammatory demyelinating polyneuropathy, among others.

Adjuvants

Adjuvants for vaccines are well known in the art. Examples include, but not limited to, monoglycerides and fatty acids (e.g., a mixture of mono-olein, oleic acid, and soybean oil); mineral salts, e.g., aluminium hydroxide and aluminium or calcium phosphate gels; oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilized water-in-oil emulsion); particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+ *M. Phlei* cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), or other DNA structures, modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array) and inert vehicles, such as gold particles. Newer adjuvants are described in U.S. Pat. No. 6,890,540, U.S. Patent Application No. 20050244420, and PCT/SE97/01003, the contents of which are incorporated herein by reference in their entirety.

In one embodiment, the immunogenic compositions as described herein further comprise an adjuvant. Examples of adjuvants include, but are not limited to QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Pharmaceutically Acceptable Carriers

In one embodiment, the vaccine as described herein comprises pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nanocapsules, liposomes, plasters, inhalation forms, nose sprays, sublingual tablets, and sustained release preparations. For examples of sustained release compositions, see U.S. Pat. Nos. 3,773,919, 3,887,699, EP 58,481A, EP 158,277A, Canadian Patent No. 1176565; U. Sidman et al., Biopolymers 22:547 (1983) and R. Langer et al., Chem. Tech. 12:98 (1982). The proteins will usually be formulated at a concentration of about 0.1 mg/ml to 100 mg/ml per application per patient.

In one embodiment, other ingredients can be added to vaccine formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the immunogenic compositions as described herein for administration must be sterile. Sterility is readily accomplished by filtration through sterile filtration membranes (e.g., 0.2 micron membranes), or by gamma radiation.

In some embodiments, the vaccine composition described herein further comprises pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts.

If the polypeptide is not soluble per se, the polypeptide can be present in the formulation in a suspension or even as an aggregate. In some embodiments, hydrophobic antigen can be solubilized in a detergent, for example a polypeptide containing a membrane-spanning domain. Furthermore, for formulations containing liposomes, an antigen in a detergent solution (e.g., a cell membrane extract) may be mixed with lipids, and liposomes then may be formed by removal of the detergent by dilution, dialysis, or column chromatography.

In some embodiments, the vaccine composition is administered in combination with other therapeutic ingredients including, e.g., interferons, cytokines, chemotherapeutic agents, or anti-inflammatory or anti-viral agents. In some embodiments, the vaccine composition as disclosed herein can be administered with one or more co-stimulatory molecules and/or adjuvants as disclosed herein.

In some embodiments, the vaccine composition is administered in a pure or substantially pure form, but it is preferable to present it as a pharmaceutical composition, formulation or preparation. Such formulation comprises polypeptides described herein together with one or more pharmaceutically acceptable carriers and optionally other therapeutic ingredients. Other therapeutic ingredients include compounds that enhance antigen presentation, e.g., gamma interferon, cytokines, chemotherapeutic agents, or anti-inflammatory agents. The formulations can conveniently be presented in unit dosage form and may be prepared by methods well known in the pharmaceutical art. For example, Plotkin and Mortimer (In 'Vaccines', 1994, W.B. Saunders Company; 2nd edition) describes vaccination of animals or humans to induce an immune response specific for particular pathogens, as well as methods of preparing antigen, determining a suitable dose of antigen, and assaying for induction of an immune response.

Formulations suitable for intravenous, intramuscular, intranasal, oral, sublingual, vaginal, rectal, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g., 0.1-2.0 M), glycine, and the like, and having a buffered pH compatible with physiological conditions to produce an aqueous solution, and rendering the solution sterile. These may be present in unit or multi-dose containers, for example, sealed ampoules or vials.

Liposomal suspensions can also be used as pharmaceutically acceptable carriers. These can be prepared according to methods known to those skilled in the art, for example, as described in U.S. Pat. No. 4,522,811.

Formulations for an intranasal delivery are described in U.S. Pat. Nos. 5,427,782, 5,843,451 and 6,398,774.

The formulations of the vaccine compositions can incorporate a stabilizer. Illustrative stabilizers are polyethylene glycol, proteins, saccharide, amino acids, inorganic acids, and organic acids which may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of 5.0-9.0, preferably within the range of 6-8.

When oral preparations are desired, the vaccine compositions can be combined with typical carriers, such as lactose, sucrose, starch, talc magnesium stearate, crystalline cellulose, methyl cellulose, carboxymethyl cellulose, glycerin, sodium alginate or gum arabic among others.

Administration and Efficacy

In some embodiments, the immunogenic compositions as described herein can be administered intravenously, intranasally, intramuscularly, subcutaneously, intraperitoneally, sublingually, vaginal, rectal or orally. In some embodiments, the route of administration is oral, intranasal, subcutaneous, or intramuscular. In some embodiments, the route of administration is intramuscular injection, or oral administration.

Vaccination can be conducted by conventional methods. For example, a displayed polypeptide can be used in a suitable diluent such as saline or water, or complete or incomplete adjuvants. The vaccine can be administered by any route appropriate for eliciting an immune response. The vaccine can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal, and analyzed for the presence of antibodies against the antigens of the immunogenic composition by ELISA (see de Boer G F, et. al., 1990, Arch Virol. 115:47-61) and the titer of these antibodies can be determined by methods known in the art.

The precise dose to be employed in the formulation will also depend on the route of administration and should be decided according to the judgment of the practitioner and each patient's circumstances. For example, a range of 25 µg-900 µg total protein can be administered monthly for 3 months.

Ultimately, the attending physician will decide the amount of protein or vaccine composition to administer to particular individuals.

In one embodiment, efficacy is determined by measuring the immunogenicity of the administered composition.

Measuring Immunogenicity

As used herein, the ability of an antigen, such as a displayed polypeptide antigen described herein, to induce an immune response, such as humoral (B-cell, antibody) and/or cell-mediated (T-cell) immune responses, is termed its "immunogenicity." An "immune response" can entail, for example, antibody production and/or the activation of immune effector cells (e.g., T cells). An antigen as described herein can comprise any subunit, fragment, or epitope of any proteinaceous molecule, including a protein or peptide of viral, bacterial, parasitic, fungal, protozoan, prion, cellular, or extracellular origin, which ideally provokes an immune response in mammal, preferably leading to protective immunity. By "epitope" is meant a sequence on an antigen that is recognized by an antibody or an antigen receptor. Epitopes also are referred to in the art as "antigenic determinants." As demonstrated herein, using the methods described herein results in increased immunogenicity or elicits a greater immune response to a given polypeptide or antigen of interest.

Accordingly, in some embodiments, a displayed polypeptide antigen elicits increased B cell responses or humoral immunogenicity relative to the B cell immune response or humoral response elicited when the polypeptide antigen is not displayed using the methods and compositions described herein. Any B cell responses elicited as a result of the methods and compositions described herein can be assayed or measured using techniques known to one of ordinary skill in the art, and include, but are not limited to, in vivo antibody production against the displayed polypeptide antigen of interest, including determination of antibody titer or quantity, antibody specificity, antibody avidity, antibody repertoire production, or any combination thereof; in vitro, ex vivo, or in vivo antigen presentation function; and developing into memory B cells after activation by antigen interaction.

In some embodiments, antibody titer can be used a measure of the humoral immunogenicity of a displayed polypeptide. As used herein, antibody titer is a measurement of how much antibody an organism, such as, for example, a human, a mouse or a rabbit, has produced that recognizes a particular epitope, expressed as the greatest dilution that still gives a positive result. ELISA is a common means of determining antibody titers, but other assays known to one of skill in the art can be used as well.

In some embodiments, antibody specificity can be used a measure of the humoral immunogenicity of a displayed polypeptide. As used herein, the term "specificity" refers to the number of different types of antigens or antigenic determinants to which an antibody or antibody fragment thereof as described herein can bind.

The specificity of an antibody or antibody fragment thereof against a given displayed polypeptide antigen can be determined based on affinity and/or avidity. The affinity, represented by the equilibrium constant for the dissociation (KD) of an antigen with an antigen-binding protein, is a measure of the binding strength between an antigenic determinant and an antigen-binding site on the antigen-binding protein, such as an antibody or antibody fragment thereof: the lesser the value of the KD, the stronger the binding strength between an antigenic determinant and the antigen-binding molecule. Alternatively, the affinity can also be expressed as the affinity constant (KA), which is 1/KD. As will be clear to the skilled person, affinity can be determined in a manner known per se, depending on the specific antigen of interest. Accordingly, an antibody or antibody fragment thereof is said to be "specific for" a first target or antigen, e.g., a displayed polypeptide of interest, compared to a second target or antigen when it binds to the first antigen with an affinity (as described above, and suitably expressed, for example as a KD value) that is at least 10 times, such as at least 100 times, and preferably at least 1000 times, and up to 10000 times or more better than the affinity with which said amino acid sequence or polypeptide binds to another target or polypeptide.

Avidity is the measure of the strength of binding between an antigen-binding molecule (such as an antibody or antibody fragment thereof) and the pertinent antigen, e.g., displayed polypeptide of interest. Avidity is related to both the affinity between an antigenic determinant and its antigen binding site on the antigen-binding molecule, and the number of pertinent binding sites present on the antigen-binding molecule. Typically, antigen-binding proteins will bind to their cognate or specific antigen with a dissociation constant (KD of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant (KA) of $10^5$ to $10^{12}$ liter/moles or more, and preferably $10^7$ to $10^{12}$ liter/moles or more and more preferably $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction is, the lower is its KD. Preferably, a binding site on an antibody or antibody fragment thereof will bind to the desired antigen, e.g., displayed polypeptide of interest, with an affinity less than 500 nM, preferably less than 200 nM, more preferably less than 10 nM, such as less than 500 μM. Specific binding of an antigen-binding protein to an antigen or antigenic determinant, e.g., displayed polypeptide of interest, can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an antibody or antibody fragment thereof to bind to a target, e.g., displayed polypeptide of interest, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. The person of ordinary skill in the art can determine appropriate conditions under which the polypeptide agents described herein selectively bind the targets described herein, e.g., using any suitable methods, such as titration of an antibody in a suitable cell binding assay.

Assays that can be used to determine binding specificity and immunogenicity of a given antibody generated against a given displayed polypeptide antigen include, but are not limited to, radioimmunoprecipitation (RIP), enzyme-linked immunoadsorbent assay (ELISA), ECL, biosensors, and bioassay. For example, ELISA is a well proven, low cost, open technology platform for detecting high affinity antibodies. Surface Plasmon Resonance (e.g., BIACORE) immunogenicity assays have been shown to be efficient in detection of low affinity antibodies, but can lose sensitivity due to the label free assay configuration and the requirement for sample dilution. It cannot be used with acid dissociation of circulating complexes. Electrochemiluminescence (ECL) immunogenicity assays are very similar to ELISA in performance and can show increased sensitivity due to the use of an electrochemiluminescent label. ECL assays also require sample dilution and a final wash step. Rapid immunogenicity assays using immunochromatographic test strips are recently developed immunogenicity assay methods that require no sample dilution and wash steps, and are thus capable of detecting both high and low affinity antibodies. Such assays are very tolerant of acid dissociated samples.

In some embodiments, the immunogenicity of a given displayed polypeptide antigen can be determined or assessed by characterization of a humoral repertoire generated in a host or subject, including, but not limited to, the full humoral repertoire. In some such embodiments, methods for characterization of a humoral repertoire include collecting multi-parametric datasets that describe the characteristics (e.g., the specificity, isotype, and apparent affinity) of the antibodies secreted from large numbers of individual primary B cells generated using the given displayed polypeptide antigens described herein in an animal model, such as a mouse or rabbit model.

A humoral repertoire, including but not limited to the full humoral repertoire, to an antigen can provide multi-dimensional information (e.g. specificities, affinities, stabilities, gene segment sequence preferences, etc) that could be considered a "profile" of a host or subject's humoral response. Quantitation of these parameters (Story et al., 2008 PNAS 105(46):17902-17907) can be used, for example, to correlate with protection from a pathogen or failure to protect. Such information could then inform vaccine design in an iterative fashion, provide the basis for a multi-parameter diagnostic assay for specific antigens, or be directly used to identify single or multiple neutralizing antibodies against a given antigen, such as a pathogen.

In other embodiments, a displayed polypeptide antigen elicits increased T cell responses or cell-mediated immunogenicity relative to the T cell immune response or cell-mediated immune response elicited when the polypeptide antigen is not displayed using the methods and compositions described herein.

Techniques for determining increased T cell responses or increased cell-mediated immunogenicity of a given displayed polypeptide antigen, include determining T cell responses to the antigen ex vivo and in vivo. To this end, antigen-presenting cells, including both professional APC (e.g., dendritic cells, macrophages, B cells), which have the ability to stimulate naive lymphocytes, and non-professional APC (e.g., fibroblasts, epithelial cells, endothelial cells, glial cells), can be incubated with effector T lymphocytes obtained from a mammal immunized against the desired displayed polypeptide antigen Unlike naive T lymphocytes, effector T lymphocytes can mediate the removal of pathogens from a host without the need for further differentiation or costimulation. Effector T lymphocytes are often referred to in the art at "armed" effector T lymphocytes, because their effector function can be triggered by antigen binding alone. CD8 T lymphocytes (also referred to in the art as cytotoxic T lymphocytes (CTL)) kill infected cells displaying cytosolic pathogen peptides on MHC Class I molecules. CD4 cells can activate macrophages with persistent vesicular pathogens whose peptides are displayed on MHC Class II molecules, and also activate B cells to produce opsonizing antibodies. CD4 cells can activate B cells that have internalized specific antigens and display peptides on MHC Class II molecules. After T cells have been incubated with antigen presenting cells expressing the given displayed polypeptide antigen, cultures are assayed for stimulation.

T cell stimulation as a measure of immunogenicity can be detected by any means known in the art. In some embodiments, culture supernatants are harvested and assayed for secretion of a polypeptide associated with activation, e.g., a cytokine, such as IFNγ, TNFα, TNFβ, interleukin-2 (IL-2), IL-4, IL-5, IL-3, IL-6, IL-10, IL-12, IL-13, IL-17, IL-33, TGFβ, or GM-CSF. Cytokine secretion in culture supernatants can be detected, e.g., by ELISA, bead array, e.g., with a LUMINEX™ analyzer. Cytokine production can also be assayed by RT-PCR of mRNA isolated from the T cells, or by ELISPOT analysis of cytokines released by the T cells. Other polypeptides associated with T cell activation, which can be assayed to detect stimulation, include perforin, granzyme, Fas ligand and CD40 ligand, CD25, and CD69. In some embodiments, proliferation of T cells in the cultures is determined (e.g., by detecting $^3$H thymidine incorporation). In some embodiments, target cell lysis is determined (e.g., by detecting T cell dependent lysis of labeled antigen presenting cells labeled with chromium). Target cell lysis assays are typically performed with CD8 T cells. Protocols for these detection methods are known. See, e.g., Current Protocols In Immunology, John E. Coligan et al. (eds), Wiley and Sons, New York, N.Y., 2011. One of skill in the art understands that appropriate controls are used in these detection methods, e.g., to adjust for non-antigen-specific background activation, to confirm the stimulatory capacity of antigen presenting cells, and to confirm the viability of lymphocytes.

Any of the assays noted above can be used by one of skill in the art to measure the immunogenicity of a displayed polypeptide relative to the same polypeptide administered in its native state, i.e., not displayed in the manner described herein. Increased immunogenicity is indicated by an at least 10% increase in immunogenicity as detected in any of these assays.

Antibody Production

The production of non-human monoclonal antibodies, e.g., murine or rat, can be accomplished by, for example, immunizing the animal with a tubular structure displaying a polypeptide and preparing hybridomas of spleen cells from the immunized animals, according to well established methods (e.g., See Harlow & Lane, Antibodies, A Laboratory Manual (CSHP NY, 1988, which is herein incorporated by reference in its entirety). Humanized forms of mouse antibodies (e.g., as produced by a hybridoma) can be generated by cloning and linking the CDR regions of the murine antibodies to human constant regions by recombinant DNA techniques. See Queen et al., Proc. Natl. Acad. Sci. USA 86, 10029-10033 (1989) and WO 90/07861 (incorporated by reference herein in their entirety). Methods for producing antibodies are known to those of skill in the art.

EXAMPLES

The methods and compositions described herein are based, in part, on the use of tubular structures as a scaffold to permit molecules of a displayed polypeptide to interact with one another (e.g., to form dimers, trimers or other multimeric, complex structures). Such proteins can be used as antigens to facilitate antibody production and/or for use in a vaccine. In the following example, the tubular structure used as a scaffold is formed by the *Vibrio cholerae* proteins VipA and VipB, however any ortholog of these proteins can also be used. The Vip proteins are known to be involved in Type VI secretion systems in bacteria.

*Vibrio cholera* Type VI Secretion System

Summary

Type VI secretion systems are bacterial virulence-associated nanomachines composed of proteins that are evolutionarily related to components of bacteriophage tails. Provided herein is data showing that protein secretion by the type VI secretion system of *Vibrio cholerae* requires the action of a dynamic intracellular tubular structure that is structurally and functionally homologous to contractile phage tail sheath. Time-lapse fluorescence light microscopy reveals that sheaths of the type VI secretion system cycle between assembly, quick contraction, disassembly and re-assembly. Whole-cell electron cryotomography further shows that the sheaths appear as long tubular structures in either extended or contracted conformations that are connected to the inner membrane by a distinct basal structure. These data support a model in which the contraction of the type VI secretion system sheath provides the energy needed to translocate proteins out of effector cells and into adjacent target cells.

Background

Secretion systems allow bacteria to transport macromolecules such as proteins out of effector cells or into either target host cells during pathogenesis or target bacterial cells during competition in various ecological settings. The type 6 secretion systems (T6SS) are encoded by a cluster of 15-20 genes that is present in at least one copy in about 25% of all sequenced Gram-negative bacteria. Although linked to virulence during host infection, recent studies showed that T6SS of *Pseudomonas, Burkholderia* and *Vibrio* species can kill prokaryotic as well as eukaryotic target host cells (Pukatzki, S. et al. *Proc. Natl. Acad. Sci. USA* 103, 1528-1533 (2006); Ma, A. T., et al., *Cell Host Microbe* 5, 234-243 (2009); Russell, A. B. et al. *Nature* 475, 343-347 (2011); MacIntyre, D. L., et al., *Proc. Natl. Acad. Sci. USA* 107, 19520-19524 (2010); Schwarz, S. et al. *PLoS Pathog.* 6, e1001068 (2010); Hood, R. D. et al. *Cell Host Microbe* 7, 25-37 (2010); Zheng, J., *PLoS ONE* 6, e23876 (2011)). T6SS$^+$ bacterial effector cells are thought to kill target cells through translocation of toxic effector proteins in a cell-cell contact-dependent process (Pukatzki, S. et al. *Proc. Natl. Acad. Sci. USA* 103, 1528-1533 (2006); Ma, A. T., et al., *Cell Host Microbe* 5, 234-243 (2009); Russell, A. B. et al. *Nature* 475, 343-347 (2011); Ma, A. T. & Mekalanos, J. J. Proc. Natl. Acad. Sci. USA 107, 4365-4370 (2010)). Little is known, however, about how T6SS transport toxic proteins through their own cell membranes or across target cell membranes.

Bioinformatic (Pukatzki, S., *Proc. Natl. Acad. Sci. USA* 104, 15508-15513 (2007)) and structural analyses (Leiman, P. G. et al. *Proc. Natl. Acad. Sci. USA* 106, 4154-4159 (2009); Pell, L. G., Proc. Natl. Acad. Sci. USA 106, 4160-4165 (2009)) have indicated that some T6SS components are structural homologues of components present in contractile phage tails. For example, secreted VgrG proteins are structural homologues of the T4 phage needle or spike complex (Pukatzki, S., Ma, et al., *Proc. Natl. Acad. Sci. USA* 104, 15508-15513 (2007); Leiman, P. G. et al. *Proc. Natl. Acad. Sci. USA* 106, 4154-4159 (2009)) and secreted Hcp is a structural homologue of a phage tail tube protein (Leiman, P. G. et al. *Proc. Natl. Acad. Sci. USA* 106, 4154-4159 (2009); Pell, L. G., *Proc. Natl. Acad. Sci. USA* 106, 4160-4165 (2009)). Another highly conserved T6SS gene product is predicted to be a homologue of gp25, a major component of the T4 phage tail base-plate (Leiman, P. G. et al. *Proc. Natl. Acad. Sci. USA* 106, 4154-4159 (2009); Leiman, P. G. et al., *Cell* 118, 419-429 (2004); Lossi, N. S., et al. *Microbiology* 157, 3292-3305 (2011)). Two T6SS gene products of *V. cholerae*, VipA and VipB, form tubular structures that can be depolymerized by another T6SS gene product, ClpV (Bonemann, G., et al., *EMBO J.* 28, 315-325 (2009); Pietrosiuk, A. et al. *J. Biol. Chem.* 286, 30010-30021 (2011); Mougous, J. D. et al. *Science* 312, 1526-1530 (2006)). Leiman et al. (Leiman, P. G. et al. *Proc. Natl. Acad. Sci. USA* 106, 4154-4159 (2009)) noted that VipA/VipB tubules visually resemble T4 contracted tail sheath and were the first to propose that a sheath-like structure might power T6SS translocation by a phage tail-like contraction mechanism. Provided herein is data indicating that T6SS-dependent secretion of Hcp and killing of *Escherichia coli* by *V. cholerae* correlates with the activity of a dynamic intracellular structure that indeed appears structurally and functionally related to contractile phage tail sheath.

Methods

Fluorescence Microscopic Imaging of the T6SS

Figure 5A:
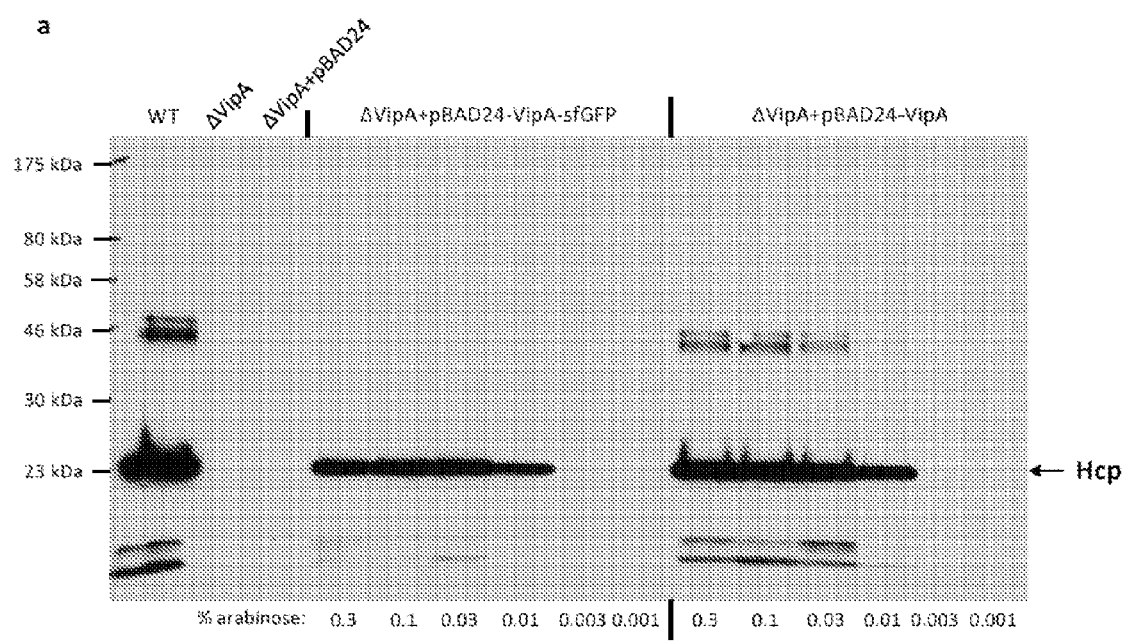
FIGS. 5A and 5B are micrographs depicting VipA-sfGFP complementation. 5A Hcp secretion—*V. cholerae* 2740-80 WT and ΔVipA carrying indicated plasmids were cultivated in presence of indicated levels of arabinose. Hcp protein was detected in cell free supernatant using a peptide specific antibody by western blot. 5B shows a sheath structure isolated from cytosol of *V. cholerae* 2740-80 WT (on the top left), ΔVipA complemented by pBAD24-VipA-sfGFP induced by 0.03% arabinose (on the top right), or ΔClpV (bottom left) by ultracentrifugation. Sheath structure was visualized by negative stain EM. F—flagellum, S—sheath.
Figures 6A, 6B, 6C, 6D, 6E, 6F, 6G:
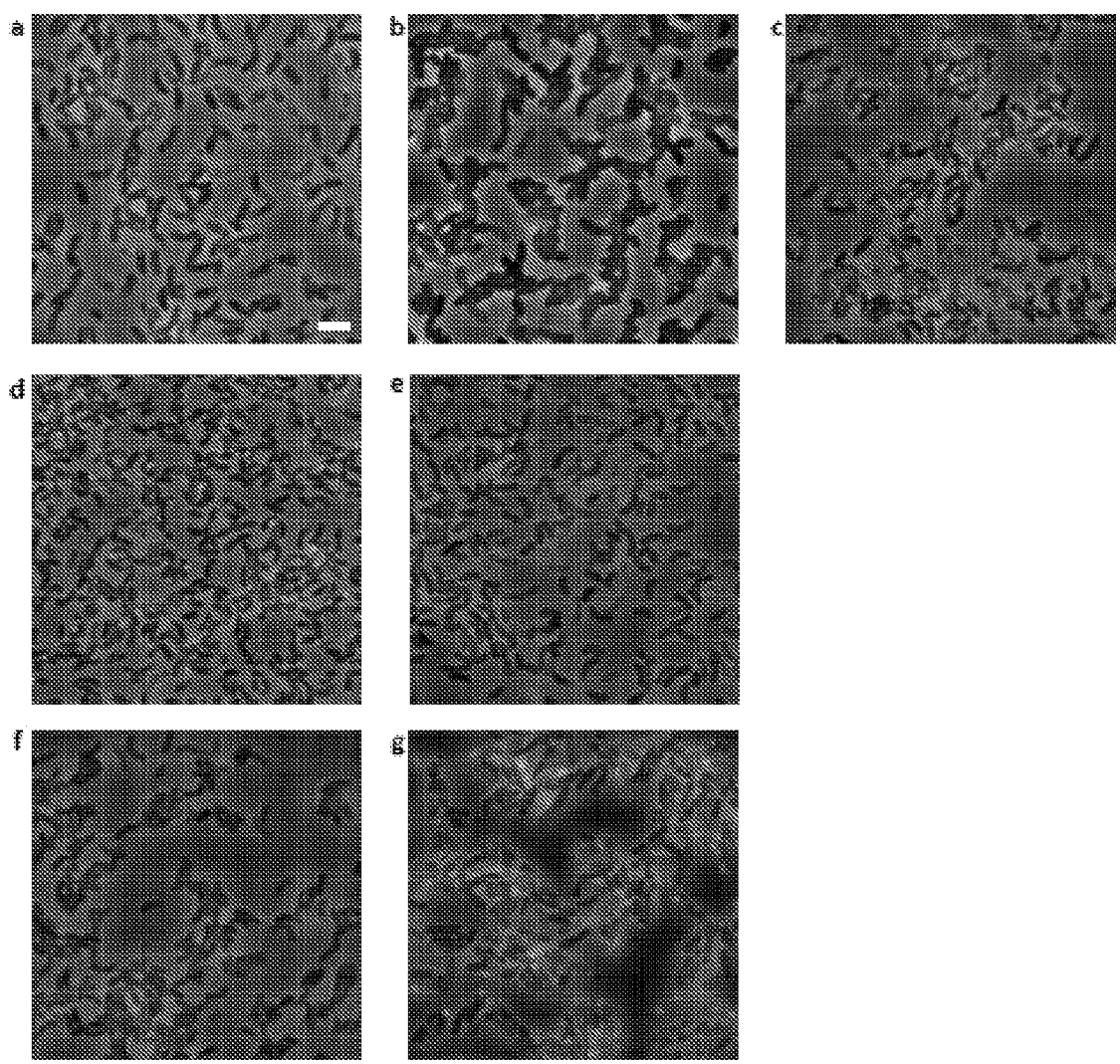
FIGS. 6A-6G are photographs depicting fluorescence microscopy of VipA fusions. All strains were cultivated under conditions described herein in the Example section. 30×30 µm field of cells is shown. Bar is 3 µm. 6A shows that VipA-sfGFP in WT cells assembles into straight and thin structures of various lengths (up to 5 per cell). 6B shows that in a ΔVipB background VipA-sfGFP is diffusely distributed in the cytosol. 6C shows *V. cholerae* 2740-80 ΔVipA+pBAD24-VipAsfGFP—both long and short VipA-sfGFP structures are detectable in the cells. 6D shows 2740-80 ΔVipA/ΔClpV+pBAD24-VipA-sfGFP—only short VipA-sfGFP structures are detectable in the cells, 6E shows that 2740-80 ΔVipA/Δgp25+pBAD24-VipAsfGFP-VipA-sfGFP is diffusely distributed in the cytosol with only rare structures detectable, 6F shows 2740-80 ΔVipA+pBAD24-VipA-mCherry2-VipA-mCherry2 forms structures similar to VipA-sfGFP, 6G shows V52 ΔVipA+pBAD24-VipA-sfGFP—similar VipA-sfGFP structures as in 2740-80 strain are visible in the cells.
Figure 7:
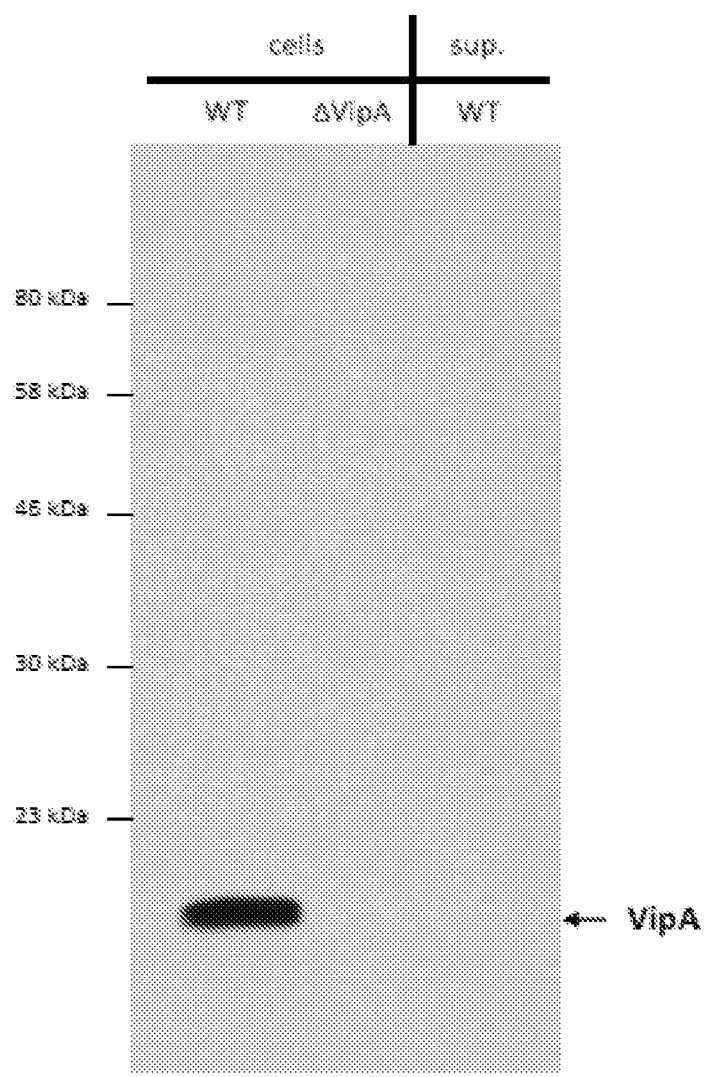
FIG. 7 is a micrograph depicting VipA localization. Wild type *V. cholerae* strain 2740-80 (WT) or derivative carrying a vipA in-frame deletion were grown to an OD600 of 1.0. Cells and supernatant fluids (sup.) were collected by centrifugation, re-suspended in SDS-PAGE sample buffer and analyzed by western blot using anti-VipA specific antibody. Absence of the signal in ΔVipA cells confirms specificity of the antibody. VipA protein was detected only in cellular fraction (cells) of WT 2740-80 strain but was undetectable in cell free supernatant (sup.).

To test the hypothesis that the T6SS apparatus is a dynamic structure, a carboxy (C)-terminal fusion of VipA protein with superfolder green fluorescent protein (sfGFP) was constructed (Pedelacq, J. D. et al., *Nature Biotechnol.* 24, 79-88 (2006)). As shown in FIG. 5A, VipA-sfGFP complements a chromosomal in-frame deletion of vipA for Hcp secretion when the fusion protein is expressed from pBAD24 plasmid to the same level as the wild-type allele. Visualization of cells expressing the functional sfGFP fusion protein by fluorescence microscopy revealed that the VipA-sfGFP fusion is associated with long straight structures in the cytosol that spread throughout the width and length of the cell. The number of visible structures in a single cell varied from 0 to 5 in wild-type background cells (FIG. 6A). Critically, these structures were not visible in vipB mutant cells (FIG. 6B), indicating that the fluorescent structures could be the T6SS sheath structures hypothesized to form in part by interaction of VipA with VipB (Leiman, P. G. et al. *Proc. Natl. Acad. Sci. USA* 106, 4154-4159 (2009)). Because VipA is not secreted and resides within cellular fractions (FIG. 7) and the expression level of VipA-sfGFP was comparable to VipA under the conditions used to visualize these sheath structures (FIG. 8), it was concluded that the fluorescent structures were within the cytosol of imaged cells.

Figure 8:
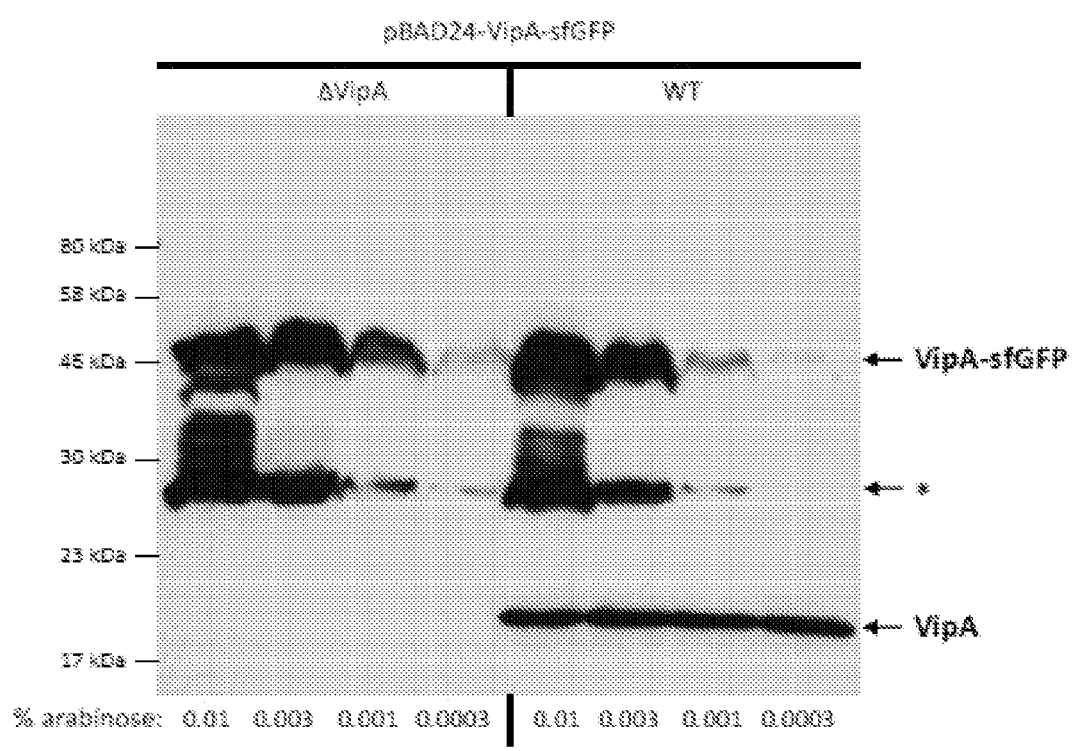
FIG. 8 is a micrograph depicting VipA-sfGFP expression level and protein stability. Plasmid pBAD24-VipA-sfGFP (which encodes the VipA-sfGFP fusion protein under control of the arabinose inducible promoter pBAD) was transferred into wild type *V. cholerae* strain 2740-80 (WT) or a derivative carrying a vipA in-frame deletion. Cells were grown to an OD600 of 1.0 in the presence or absence of the indicated levels of arabinose, collected by centrifugation, re-suspended in SDS-PAGE sample buffer and analyzed by western blot using anti-VipA specific antibody. The full length VipA-sfGFP fusion protein migrates at approximately 46 kDa, and WT VipA at 19 kDa. The asterisk indicates bands corresponding to breakdown fragments of VipA-sfGFP that retain VipA epitopes.
Figure 10:
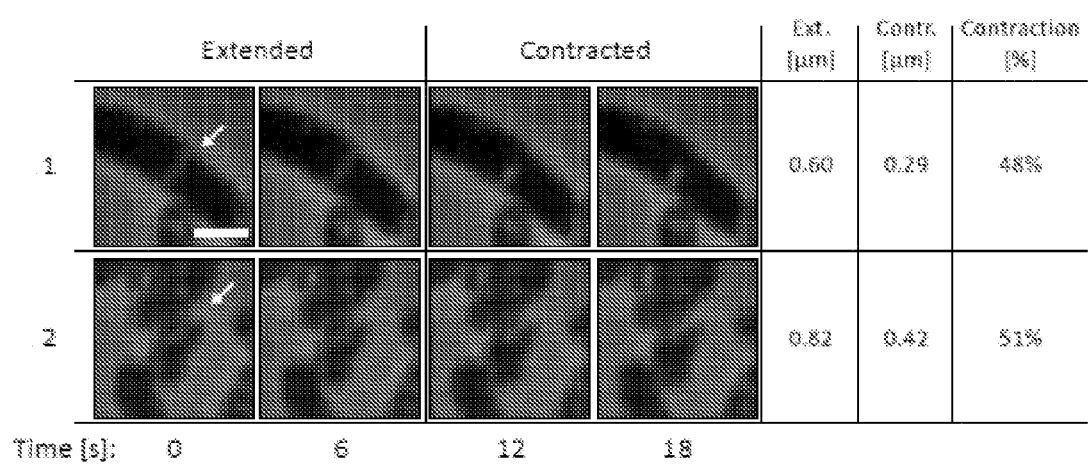
FIG. 10 is a micrograph depicting the measurement of contraction in a culture of *V. cholerae* 2740-80 ΔVipA strain carrying plasmid pBAD24-VipA-sfGFP induced by arabinose and imaged as described herein in the Examples. Individual 3×3 μm frames from a time-lapse imaging with a frame rate of 6 sec per frame are shown. 2 frames of sheath in an extended conformation and 2 frames of sheath in a contracted conformation are shown to illustrate the change in length. Bar shown on the first frame of the first timelapse is 1 μm long. The length of an extended and a contracted sheath was estimated by analysis of an intensity of the fluorescence signal alone.

Time-lapse imaging revealed these putative sheath structures to be highly dynamic. As shown in FIG. 1A, the VipA-sfGFP labelled sheaths extended within tens of seconds in different subcellular locations and then contracted and disassembled also within tens of seconds. Most of the extended sheath structures visible in cells stretched from one lateral side of the cell to the other, perpendicular to the membrane, and thus had lengths approximately equal to the width of the cell (about 0.75-1 µm). As shown in FIG. 1A, these sheaths assembled at speeds of approximately 20-30 s $\mu m^{-1}$. Contraction was very fast, occurring in approximately 5 ms or less (unresolvable at frame rates of approximately 200 frames per second; see FIGS. 1B and 1C. Sheaths contracted to about 50% of their extended length (FIG. 10), and then disassembled over the next 30-60 s (FIG. 1A). The disassembly of the contracted sheath is most probably a ClpV-dependent event because ClpV is known to disassemble VipA/VipB tubules in vitro in the presence of ATP (Bonemann, G., et al. *EMBO J.* 28, 315-325 (2009)) and clpV mutants do not disassemble VipA-sfGFP-labelled contracted sheaths (FIG. 6D). A similar number of VipA-sfGFP-labelled sheaths were seen in strains 2740-80 and V52 and at various levels of VipA-sfGFP expression (FIGS. 6C, 6G and 8). The sheaths in wild-type cells displayed the same extension-contraction-disassembly cycles as sheaths observed in complemented vipA mutant cells and when mCherry2 (Cho, H. et al., *Proc. Natl. Acad. Sci. USA* 108, 3773-3778 (2011)) was substituted for sfGFP (FIG. 6F). Thus, the dynamic behaviour observed is not just a property of sheaths that contain exclusively VipA-sfGFP fusion protein, but also of sheaths composed largely of wild-type VipA or other VipA fusion proteins. VCA0109 encodes a member of a family of phage base-plate proteins (Leiman, P. G. et al. *Proc. Natl. Acad. Sci. USA* 106, 4154-4159 (2009)). In a VCA0109 deletion background most of the VipA-sfGFP was dispersed in the cytosol with only a rare, VipA-sfGFP-containing structure ever visible (FIG. 6E). VCA0109 therefore plays a critical role in the formation of functional T6SS sheaths.

Electron Cryotomographic Imaging of the T6SS

Figures 11A, 11B, 11C, 11D:
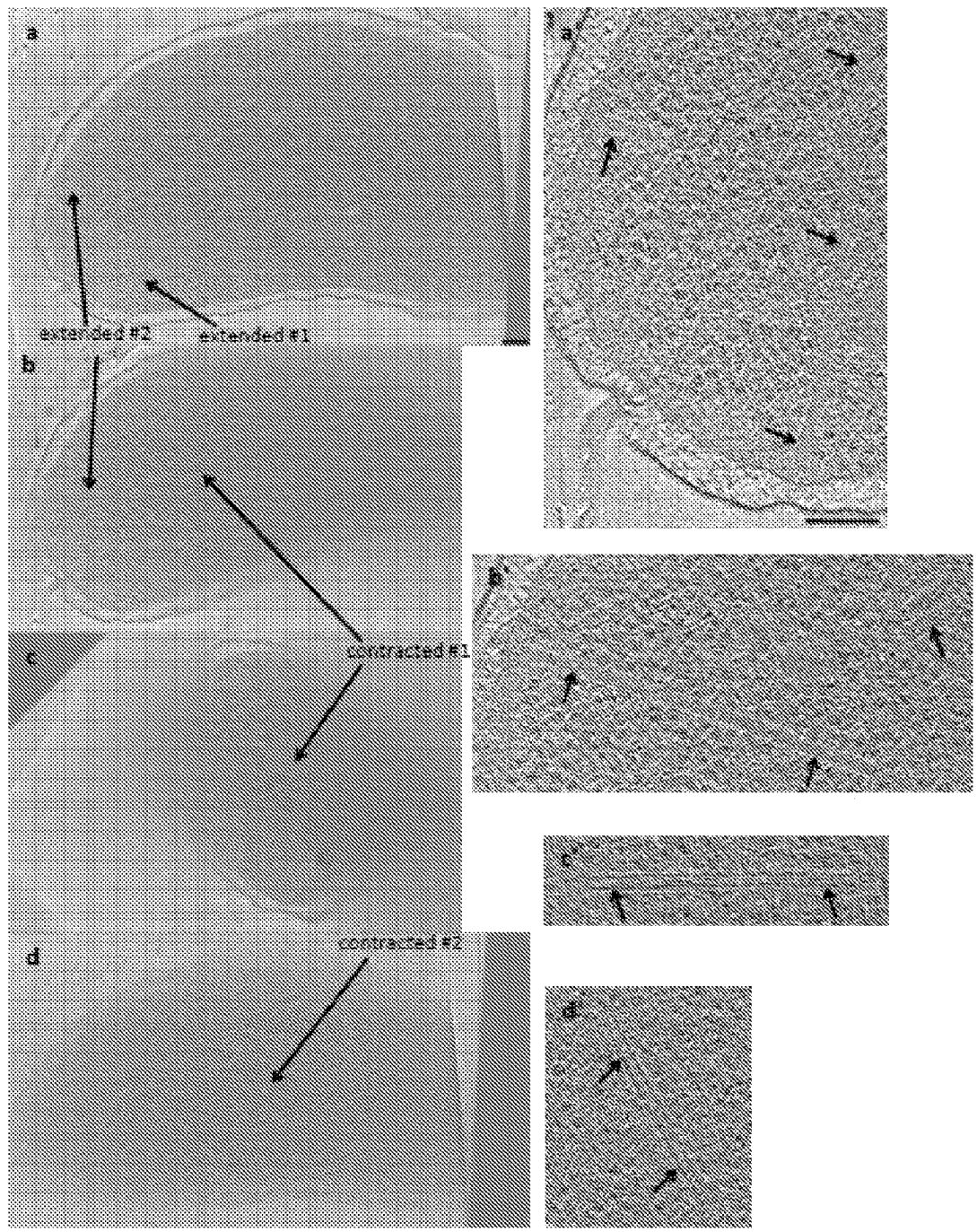
FIGS. 11A-11D are micrographs showing a cell with multiple Type 6 Secretion System (T6SS) visible. Various cryotomographic slices (19-nm thick) through the 3-D reconstruction of a single wild-type cell are shown along planes where T6SS structures are present. Two extended and two contracted structures can be seen (arrows). Bars represent a length of 100 nm. Bar in (11A) applies to (11A-11D), bar in (11A') applies to (11A'-11D').

To visualize the sheaths directly, wild-type and mutant whole cells were imaged with electron cryotomography (ECT). ECT has been shown to preserve and reveal bacterial cytoskeletal structures directly in three dimensions in a near-native, life-like state (Pilhofer, M. et al., *Methods Cell Biol.* 96, 21-45 (2010)). ECT analyses of wild-type 2740-80 cells showed straight, tubular structures which appeared to exist in two different conformations: a longer, thinner 'extended' conformation (FIGS. 2A-D) and a shorter, wider, 'contracted' conformation (FIGS. 2E-2H). Both structures were oriented roughly perpendicular to the cytoplasmic membrane and were clearly located exclusively in the cytosol. Tubular structures were observed in 26 of 90 imaged wild-type cells. Some cells exhibited more than one tubule and on occasion both extended and contracted conformations were seen in the same cell (FIG. 11). No tubular structures were observed in a vipB mutant (0 of 53 cells), a VCA109 mutant (0 of 10 cells) and a VCA0109/ClpV double mutant (0 of 8 cells), indicating that both types of tubule are T6SS-related structures.

Figures 2A, 2B, 2C, 2D, 2E, 2F, 2G, 2H:
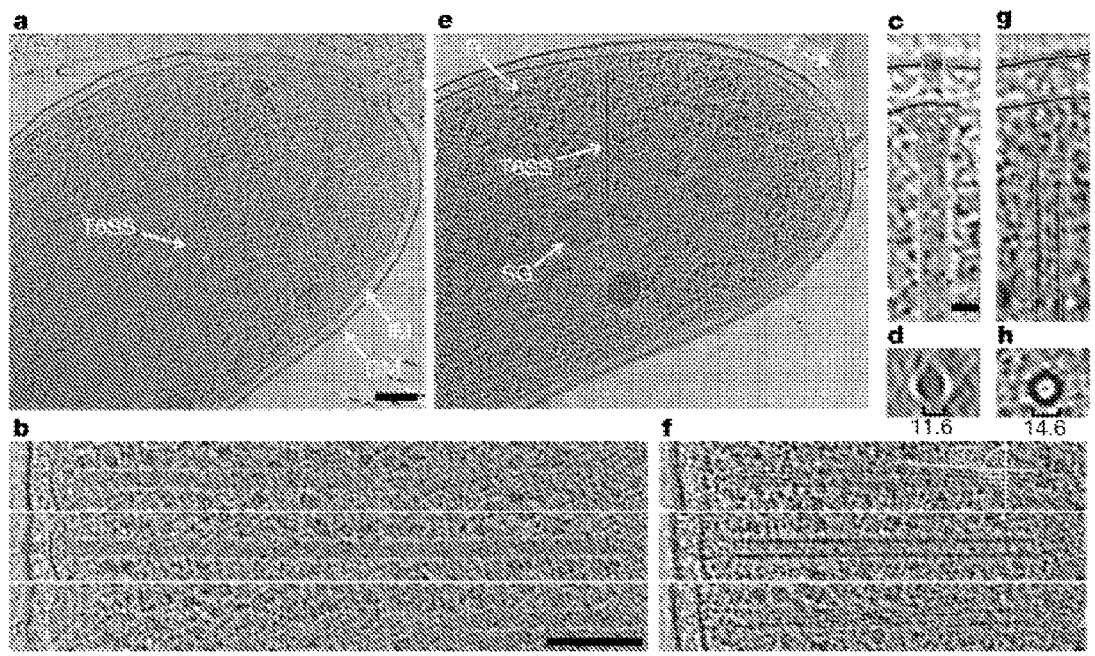
FIGS. 2A-2H Electron cryotomographic imaging of T6SS structures inside intact cells. Shown are different tomographic slices (19 nm in 2A, 2E, 2C, 2G; 9.5 nm in 2B, 2F; 190 nm in 2D, 2H) of an extended (2A-2D) and a contracted (2E-2H) structure imaged in two different wild-type cells (contracted/extended structures, T6SS; IM, inner membrane; OM, outer membrane; F, flagellum; R, putative ribosome; SG, polyphosphate storage granule). 2B, 2F, Each part shows three slices at the same orientation but at different z-heights. Compared with extended structures, contracted structures are shorter (2B, 2F), have a helical surface pattern (pitch angle 87°) and a smaller diameter (indicated in the perpendicular views in 2D, 2H). 2C, 2G, Segmentations of densities observed in the extended (2C) and contracted (2G) structures. Densities shown in 2H originate from a contracted structure from a different tomogram. Segmented are putative densities corresponding to sheath (green), base plate (pink and yellow) and membranes (blue). Scale bars: 2A, 100 nm (applies to 2A, 32E); 2B, 100 nm (applies to 2B, 2F); 2C, 20 nm (applies to 2C, 2D, 2G, 2H).
Figures 12A, 12B, 12C, 12D:
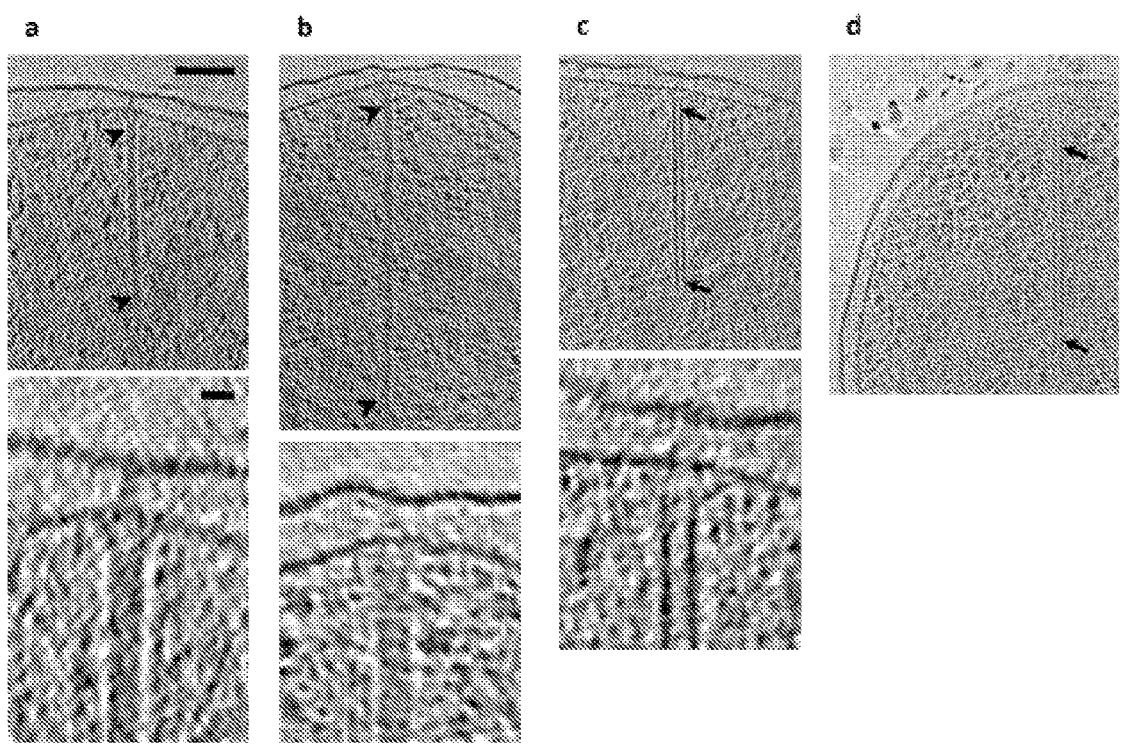
FIGS. 12A-12D are micrographs depicting additional examples of T6SS structures. Extended (12A, 12B arrowheads) and contracted (12C, 12D arrows) T6SS structures found in wild type cells. The baseplate/spike regions are shown enlarged (lower panels in 12A-12C). The slices shown are 19-nm thick. Scale bars 100 nm in overviews, 10 nm in enlarged views.
Figures 13A, 13B:
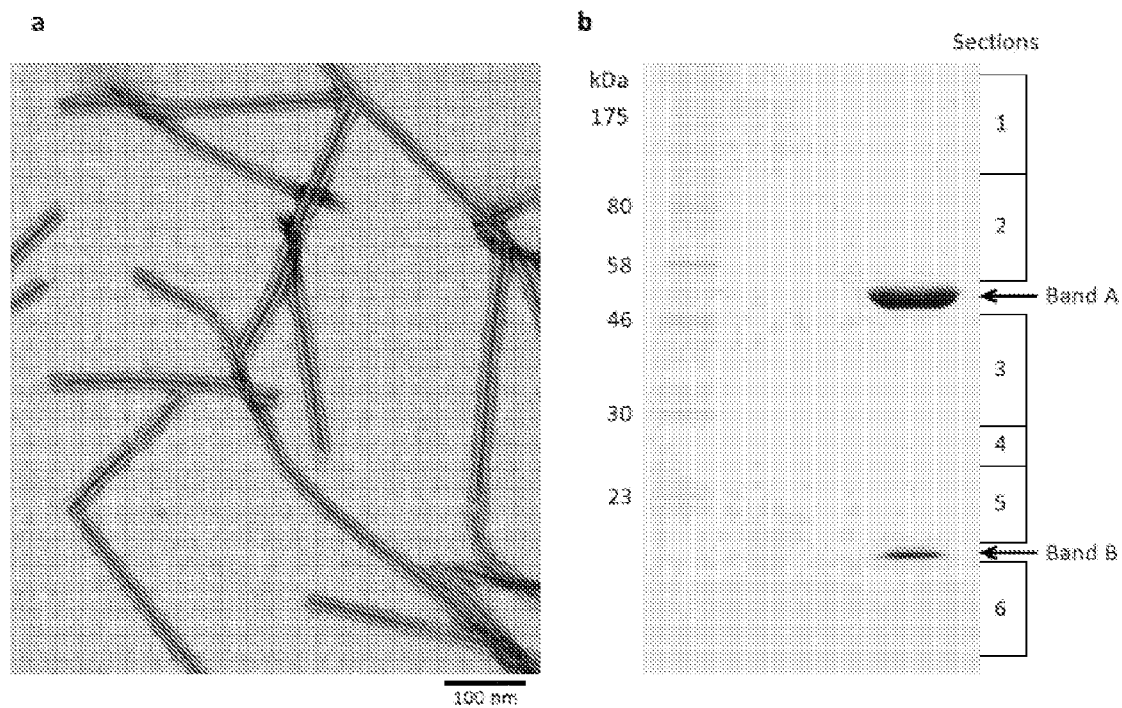
FIGS. 13A-13B are micrographs depicting a purified sheath using EM and SDS-PAGE analysis. Sheaths isolated from non-flagellated *V. cholerae* 2740-80 were purified from cytosolic proteins by three rounds of ultracentrifugation. 13A shows a sheath visualized by EM after uranyl formate negative staining 13B shows a sample of the purified sheath (about 20 μg) separated by 10-20% pre-cast polyacrylamide gel. The gel was stained by Coomassie blue R-250 and after destaining two visible bands and 6 sections of the gel were cut out and protein content was determined by MS. Band A contained mostly VipB protein and Band B mostly VipA protein.

Consistent with the dynamic sheaths in the two-dimensional fluorescence projection images, the extended and contracted tubes seen in the three-dimensional cryotomograms had lengths of 667±83 nm (n=13) and 372±56 nm (n=16), respectively. Although extended tubes had diameters of 11.6±0.7 nm, dense interiors, and a homogeneous surface, it was observed that contracted tubes were thicker (14.6±0.7 nm diameter), hollow, and had helical ridges (87° pitch angle) spaced 6 nm apart (FIG. 2). The tubular structures of both conformations were usually found with one end in close proximity to the cytoplasmic membrane in a near-perpendicular orientation (FIG. 2 and FIG. 12). The tubes did not contact the membrane directly, however, but instead appeared to be connected to it by a flared bell-shaped base (FIG. 2C, 2G). Distal to the flared base of extended, but not contracted tubes, there was an additional conical-shaped density (FIG. 2C) that crossed the periplasm and protruded through the outer membrane. Given that various T6SS components have been localized to the inner membrane, periplasm and outer membrane including a lipoprotein unique to T6SS as well as proteins related to orthologues IcmF, DotU, and OmpA in other organisms (Aschtgen, M. S. et al., *J. Bacteriol.* 190, 7523-7531 (2008); Aschtgen, M. S. et al., *Virulence* 1, 535-540 (2010); Aschtgen, M. S. et al., *Mol. Microbiol.* 75, 886-899 (2010)), the inventors proposed that all these densities simply be called the 'T6SS base plate' complex.

Purification of T6SS Sheath from *V. cholera*

Figures 3A, 3B, 3C, 3D, 3E:
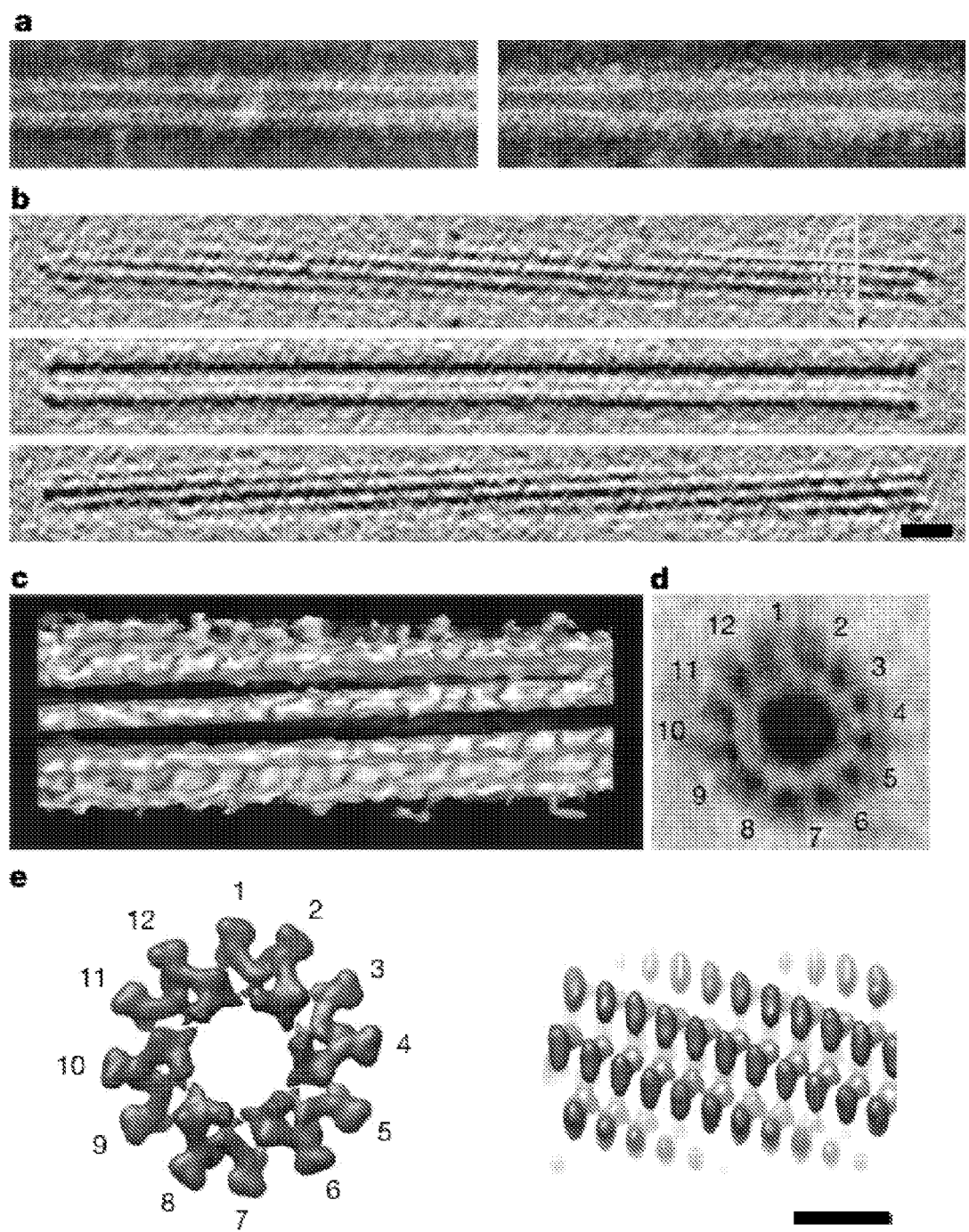
FIGS. 3A-3E Images of purified VipA/VipB sheaths and comparison with phage tails. Negative staining (3A) images of purified wild-type sheath (left) and VipA-sfGFP-labelled sheath (right) are highly similar except for flared extra densities on the outside of the VipA-sfGFP-labelled structure. Cryotomograms of wild-type sheath (3B, showing three 12.6-nm slices at different z-heights) were highly similar to contracted structures imaged in vivo (FIG. 2F). Note the matching surface pitch angle of 87° seen in tomographic slices (3B) and an isosurface of a subtomogram average (3C). The negatively stained perpendicular view of a purified wild-type sheath showed the characteristic 'cogwheel' like structure with 12 paddles (3D) and is similar to the perpendicular view of a contracted T4 phage sheath (3E, left; two rings of six gp18 subunits, created in Chimera from EMDB 1086 map). Similar to T6SS sheath (c), also the surface of the contracted T4 phage sheath appears helical (3E, right) though with a different pitch angle. Scale bars: 3B, 20 nm (applies to 3A, 3B); 3E, 10 nm (applies to 3C-3E. Note that protein densities appear white in negative stain images and black in cryotomograms.
Figure 5B:
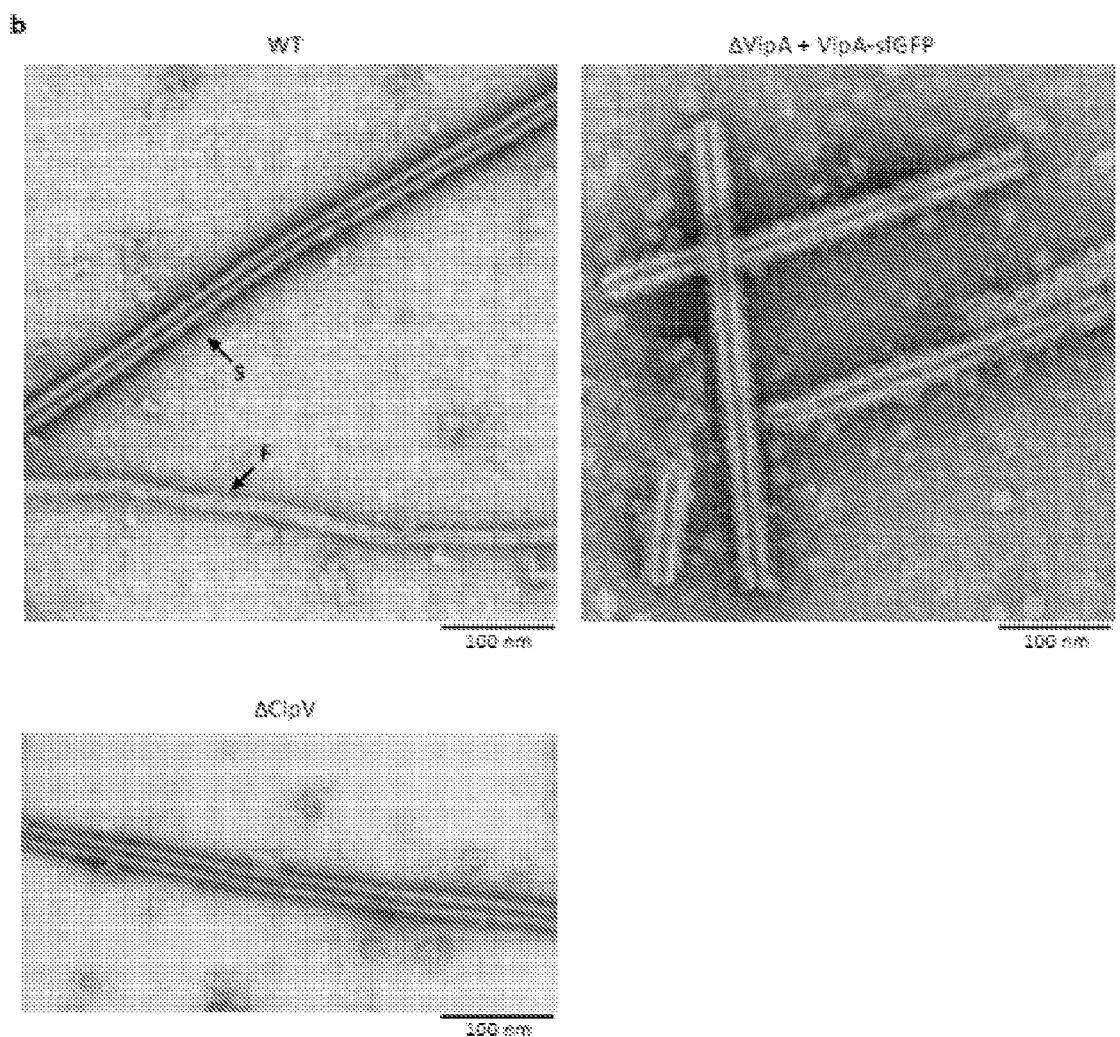

To prove that the dynamic fluorescent structures observed in VipA-sfGFP expressing cells and the tubes observed by ECT were indeed T6SS sheath-related structures, the corresponding structures were purified from disrupted cells. Negative stain electron microscopic analysis of macromolecular fractions purified from cell lysates of wild-type cells revealed straight, hollow tubular structures similar to, but more uniform than, the VipA/VipB tubules produced previously in *E. coli* (Bonemann, G. et al., *EMBO J.* 28, 315-325 (2009)) and distinct from the *V. cholerae* flagellum (FIG. 3A left and FIG. 5B left). No sheath-like structures were detected in identically prepared samples from mutants defective in VipA or VipB, although flagella were visible. Electron microscopic analysis of sheath preparations made from the VipA-sfGFP complemented vipA mutant strain revealed sheath structures similar to those produced by wild-type cells except that a diffuse coat was laterally displayed on the filament's surface, probably corresponding to the sfGFP moiety on the fusion protein (FIG. 3A right and FIG. 5B right).

Figure 9:
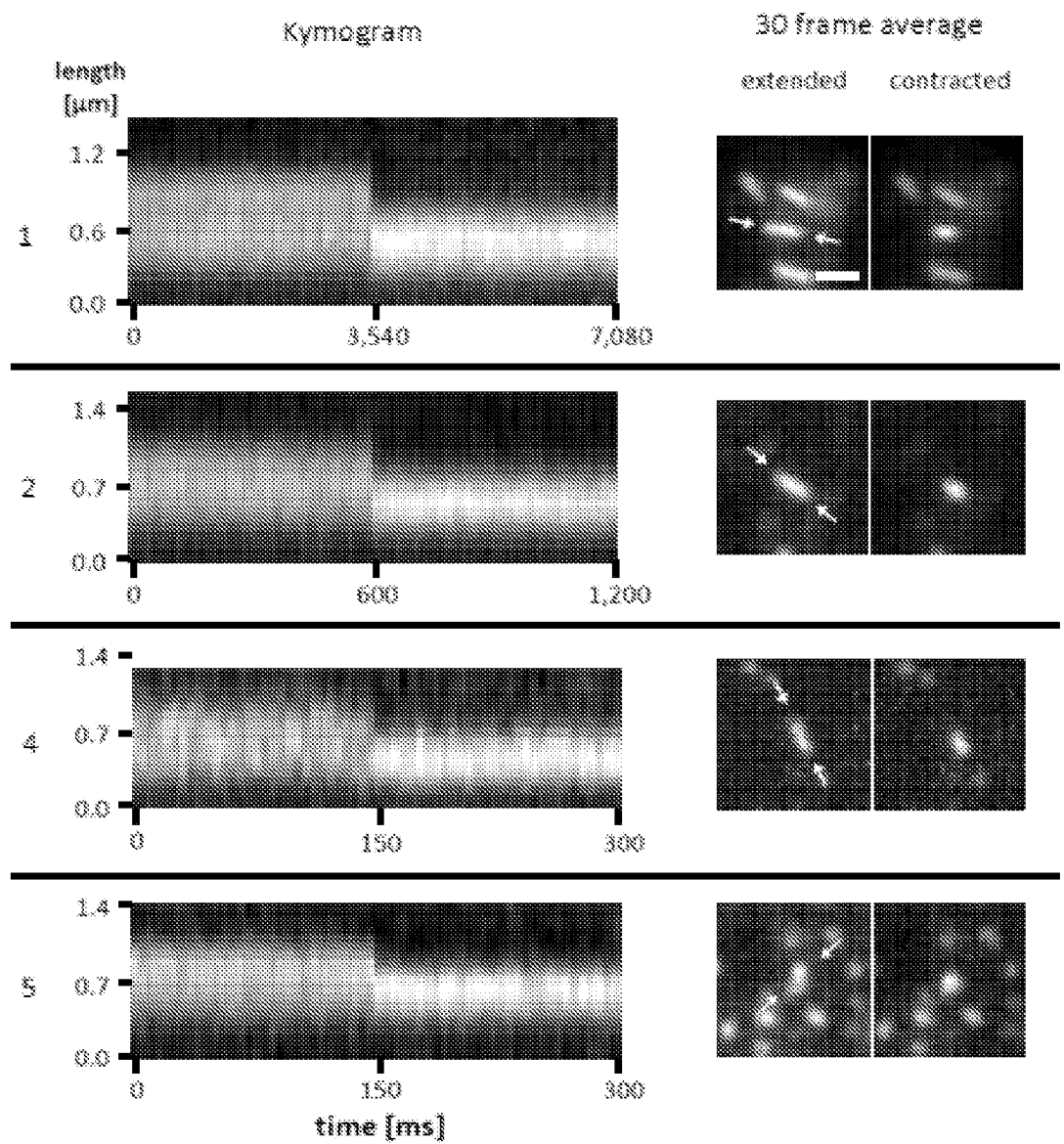
FIG. 9 is a micrograph depicting high speed imaging of sheath contraction. Kymograms on the left are illustrating rapid change in the length of VipA-sfGFP structure. Projection of signal intensity in time along the axis of the maximal intensity on an extended structure (30 frame average shown on the right) showing a contraction in length and increase in maximal intensity of the contracted structure (30 frame average shown on the right). Arrows indicate contracting VipA-sfGFP structure and mark start and end of a line for generating the kymogram. Gaussian blur filter (sigma radius=1) was applied to individual frames prior to generating the kymogram for events number 2, 4 and 5. Event 1 was analyzed at speed of 8.5 frames per second (50 ms exposure), event 2 at 50 frames per second (20 ms exposure), and event 4 and 5 at 200 frames per second (5 ms exposure). Bar shown on the first average frame is 1 μm long.

To identify proteins that were associated with these sheaths, the structures were purified from a non-flagellated mutant (flgG) of *V. cholerae* 2740-80 (FIG. 9A). Two major proteins were enriched in these preparations with apparent molecular masses of 55 and 20 kDa, respectively (FIG. 9B). Mass spectrometry analysis revealed that the 55 kDa band was VipB and the 20 kDa band was VipA. Interestingly, four additional T6SS proteins were also identified in the sheath samples: ClpV, VCA0109 (a gp25-like protein), and two other proteins within the T6SS gene cluster encoded by genes VCA0111 and VCA0114. ClpV was recently shown to interact directly with VipB, most strongly in its polymerized state with VipA (Pietrosiuk, A. et al. *J. Biol. Chem.* 286, 30010-30021 (2011)). As noted earlier, VCA0109 is a homologue of T4 base-plate protein gp25 (Leiman, P. G. et al. *Proc. Natl. Acad. Sci. USA* 106, 4154-4159 (2009)) and a T6SS 25-like protein was recently shown to localize to the cytoplasm of *P. aeruginosa* (Lossi, N. S. et al., *Microbiology* 157, 3292-3305 (2011)). The function of VCA0111 and VCA0114 are currently unknown, but they are essential components of the *V. cholerae* T6SS (Zheng, J. *PLoS ONE* 6, e23876 2011)).

Figures 14A, 14B, 14C, 14D, 14E, 14F, 14G:
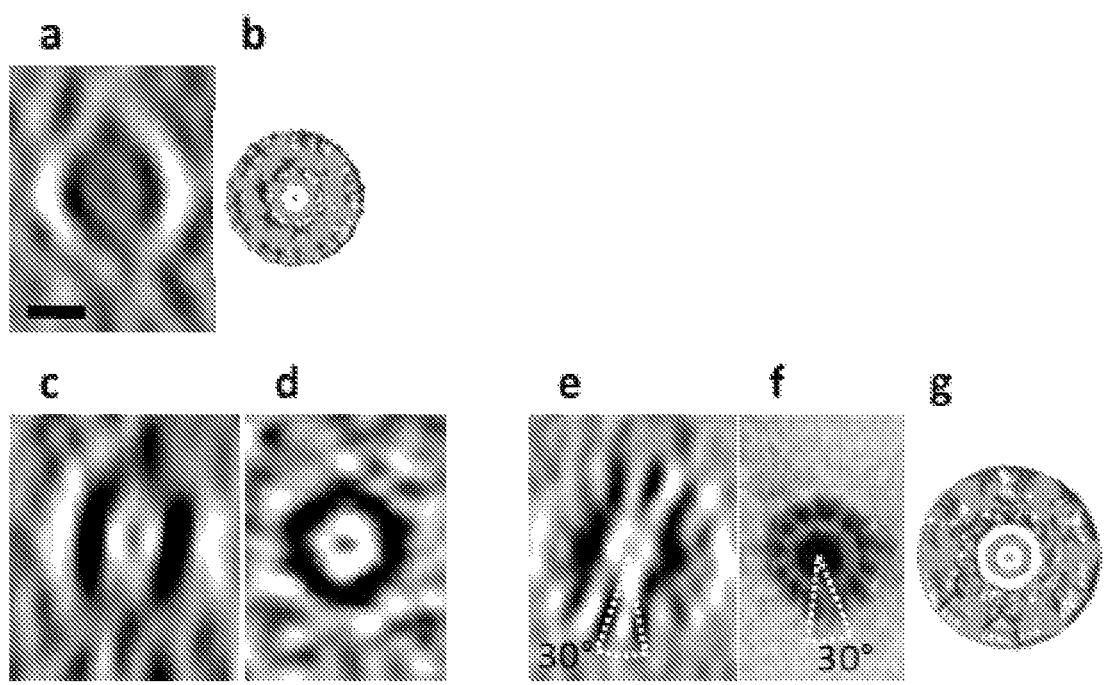
FIGS. 14A-14G depict cross-sections through T6SS and phage sheaths. Top row: extended structures, bottom row: contracted structures. 14A, 14C and 14D show 190-nm cryotomographic slices through T6SS sheaths within intact cells. 14E shows a 19-nm cryotomographic slice through a purified T6SS sheath. 14F shows a projection image of a negatively stained T6SS sheath 14B and 14G are cross-sections through space-filling models of T4 phage sheath (created in Chimera from EMDB 1086 map). While panels 14A, 14C, and 14E are of sheaths that lay parallel to the sample grid, 14D is of a sheath that was oriented perpendicular. Because useful EM images cannot be obtained of samples tilted further than ~65°, there is a "missing wedge" of data in reciprocal space that manifests as a blurring of the reconstruction perpendicular to the sample grid (the "z" direction). Thus tubular objects lying in the plane of the sample look like parentheses facing each other in slices perpendicular to the grid ("xz" slices), with the "top" and "bottom" of the ring missing (panels 14A, 14C and 14E). Panel 14D therefore gives a superior view, since it is an "xy" slice without blur. In addition to the missing wedge, electron cryotomograms also suffer from the point-spread-function of the microscope, which like a low-pass-filter causes densities to appear as dark regions surrounded by bright fringes, or "halos". Thus in panels 14C and 14D it can be seen that contracted tubes are hollow, since they have bright interiors. Comparing panels 14C and 14A, however, reveals that extended tubes (panel 14A) are filled. This is also made clear in panel 14A itself through the difference in intensity immediately outside the tube (bright white) and the interior (medium grey). The medium grey interior is the superposition of density there with the white fringe from the sheath. Panel 14E has higher resolution and clarity (signal-to-noise-ratio) because it is of a purified sheath frozen in a very thin film of dilute buffer. As a result, the features within a much thinner slice (19-nm) are already clear, revealing the helical "paddles" that wrap around the sheath and are therefore averaged out in thicker slices (panels 14C and 14D). Panels 14E and 14F show that the paddles are spaced every 30°, corresponding to 12 around the circumference of the tube. Again because of the missing wedge effect, the central ring density is apparent on the sides (where its tangent is parallel to z), but the thin flat paddles appear best at the top and bottom (where their faces are parallel to z). The fact that there are 12 paddles around the T6SS (just as there are in contracted phage tails) is made even more clear in the negatively-stained sheath fragment imaged down its long axis (panel 14F). In negatively-stained images, the protein is light and the stain inside the tube and between the paddles is dark. Bar, 10 nm.

The VipA/VipB sheath preparations purified from wild-type 2740-80 cells were also imaged by ECT (FIG. 3B, 3C), by which they were recognized as the contracted tubes seen previously inside cells (14.4 nm diameter, hollow interior, and helical surface ridges spaced 6 nm apart with pitch angle 87°). Interestingly, in addition to helical surface ridges, purified sheaths exhibited cogwheel-like cross-sections with 12 surface 'paddles' per rotation (FIG. 3D, seen most clearly after negative staining) and thus are structurally similar to contracted T4 phage sheaths (Leiman, P. G. et al., *Cell* 118, 419-429 (2004)) (FIG. 3E and FIG. 14). It is concluded that the two tubular structures seen in vivo by ECT correspond to extended and contracted states of the dynamic VipA-sfGFP-labelled T6SS sheath that was visualized using fluorescence light microscopy.

Figure 15A:
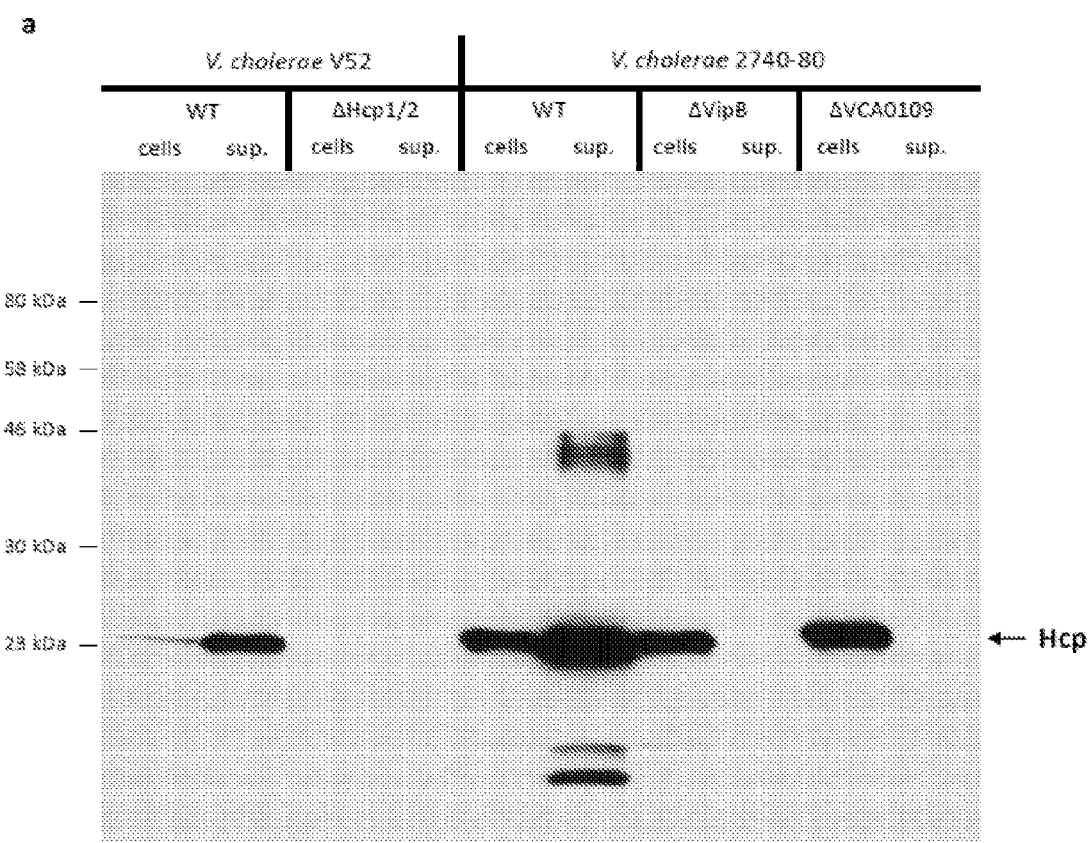
FIGS. 15A and 15B are micrographs depicting secretion of Hcp by T6SS. Wild type strains V52 and 2740-80 as well as indicated mutants with deletion of both copies of the Hcp genes, vipB or VCA109 genes were grown as described herein and protein samples were prepared for western blot analysis. Hcp protein was detected in a cell lysate (cells) and a cell free supernatant (sup.) using a peptide specific antibody. Absence of the signal in V52 ΔHcp1/2 cells confirms specificity of the antibody. 15B shows quantification of *E. coli* killing by *V. cholerae*. *E. coli* was mixed with *V. cholerae* in a ratio 1:10 and spotted on a LB plate. After 2 or 4 hours of incubation at 37° C. the cells were washed from the agar, serially diluted and spotted on a plate to select for *E. coli* or *V. cholerae*.

Contractile phage tails consist of a contractile outer sheath and an inner tube that is projected into a target host cell during phage infection (Kostyuchenko, V. A. et al. *Nature Struct. Mol. Biol.* 12, 810-813 (2005)). The T6SS of *V. cholerae* is known to possess antibacterial activity against *E. coli* that correlates with its ability to secrete the T6SS substrate protein Hcp (MacIntyre, D. L. et al., *Proc. Natl. Acad. Sci. USA* 107, 19520-19524 (2010); Zheng, J. et al., *PLoS ONE* 6, e23876 (2011)). As shown in FIGS. 5A and 15A, *V. cholerae* strain 2740-80 secretes abundant Hcp and this secretion is completely abolished by deletion of T6SS genes vipA, vipB and VCA0109 (which encodes a gp25-like protein), as has been previously shown for *V. cholerae* strain V52 (MacIntyre, D. L. et al., *Proc. Natl. Acad. Sci. USA* 107, 19520-19524 (2010); Zheng, J. et al., *PLoS ONE* 6, e23876 (2011)). Although the material inside the extended tubule visualized with ECT (FIG. 2D and FIG. 14A) could not be resolved as a separate 'inner tube' per se, its diameter was similar to the diameter of Hcp tubes described at either the crystallographic or microscopic level (Mougous, J. D. et al. *Science* 312, 1526-1530 (2006); Ballister, E. R. et al., *Proc. Natl. Acad. Sci. USA* 105, 3733-3738 (2008)). Furthermore, contracted tubes were clearly hollow (FIG. 2H and FIG. 14C-14F). Thus, the inventors proposed that the thinner extended tubule found in whole cells is an uncontracted 'extended T6SS sheath' whose VipA/VipB subunits are probably wrapped around a thinner inner tube composed of Hcp protein. Unfortunately, the uncontracted, extended T6SS sheaths could not be purified from *V. cholerae* cells for further analysis, perhaps because of spontaneous sheath contraction during cellular disruption and purification. Because Hcp was not found in purified contracted T6SS sheaths, it was concluded that the postulated inner Hcp tube of extended sheaths is largely expelled from the cell at the moment of contraction.

ClpV and T6SS Sheath Recycling

Figure 1B:
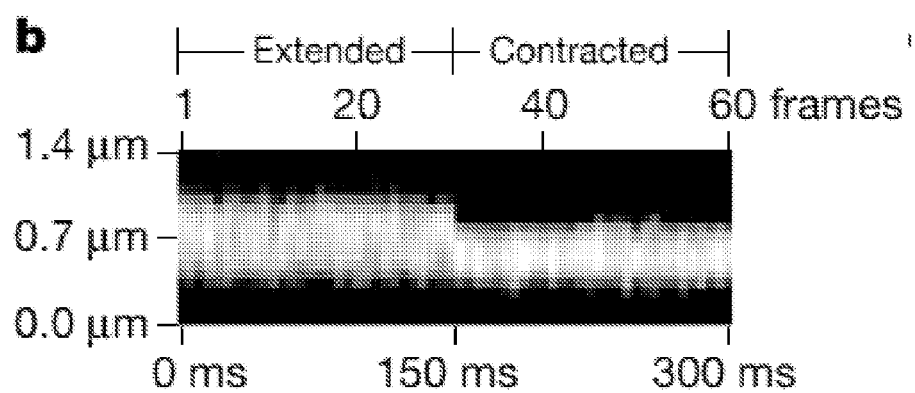
Figure 1C:
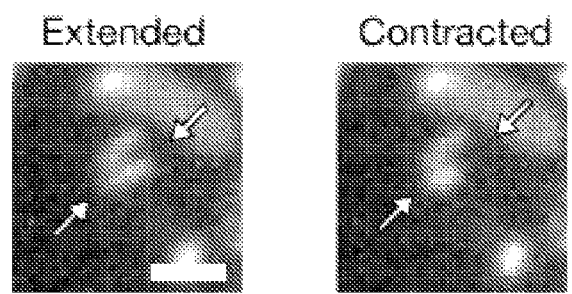
Figure 15B:
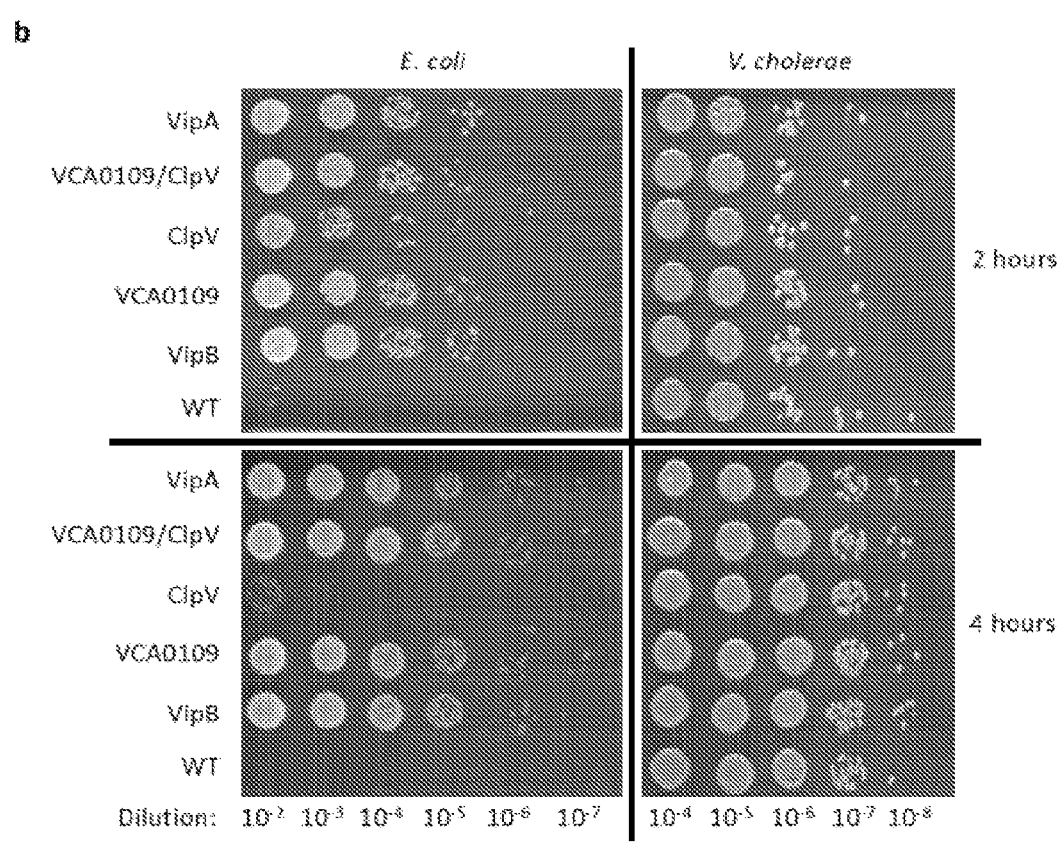

Like strain V52 (MacIntyre, D. L. et al., *Proc. Natl. Acad. Sci. USA* 107, 19520-19524 (2010); Zheng, J., et al., *PLoS ONE* 6, e23876 (2011)), *V. cholerae* 2740-80 also rapidly kills *E. coli* when co-cultivated on agar in a vipA-, vipB-, and VCA0109-dependent fashion (FIG. 15B). Consistent with published results in strain V52 (Zheng, J., et al., *PLoS ONE* 6, e23876 (2011)), the ClpV mutant of 2740-80 showed 90% loss of T6SS-dependent killing in 2 h assays but retained bacteriocidal activity well above background during incubation for 4 h. Thus, ClpV is not essential for T6SS function in *V. cholerae*. Because ClpV has been shown to disassemble in vitro a tubular structure that is produced in *E. coli* expressing VipA and VipB (Bonemann, G. et al., *EMBO J.* 28, 315-325 (2009)), the inventors asked whether ClpV affected the dynamics of T6SS sheath imaged with the VipA-sfGFP fusion. No polymerization or disassembly events were observed in the ClpV mutant background; rather, it was found that most VipA-sfGFP existed in static punctate structures (FIG. 2D), which were probably contracted T6SS sheaths because ClpV mutants produce contracted sheath-like structures (FIG. 1B).

Figures 4A, 4B, 4C, 4D:
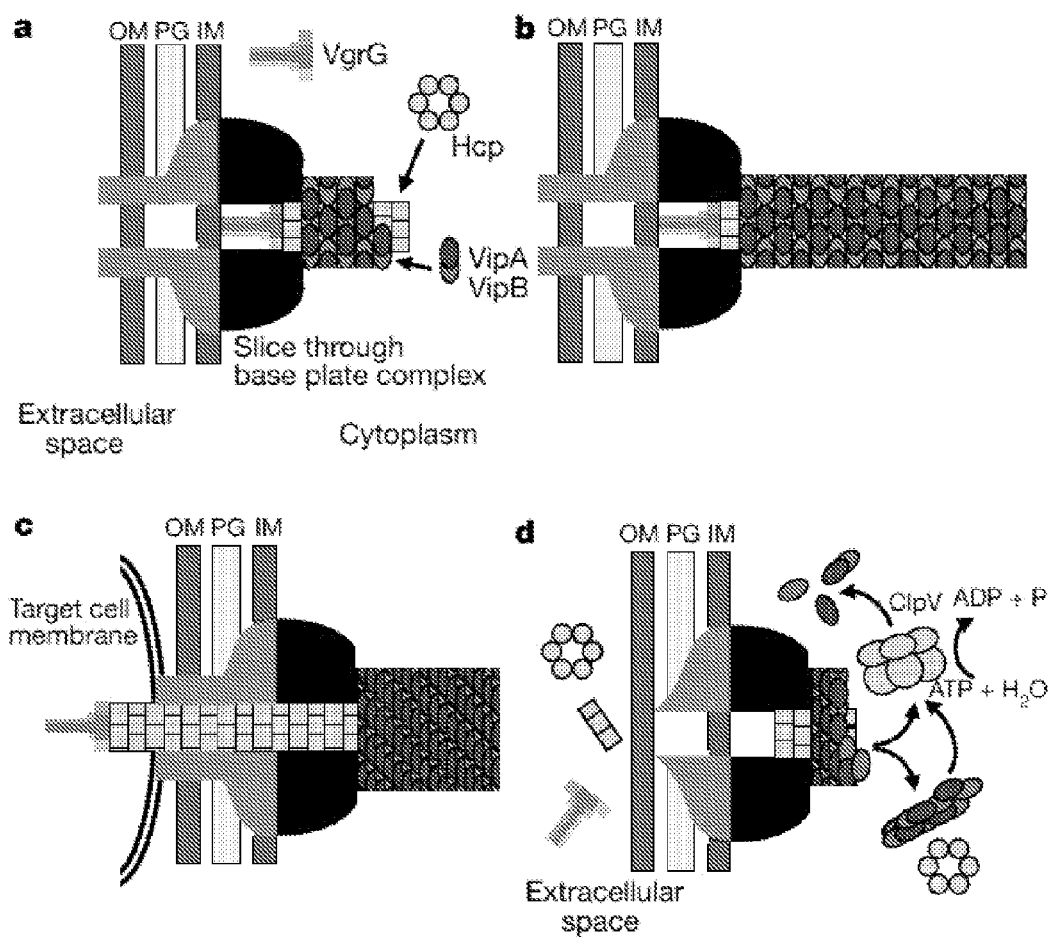
FIGS. 4A-4D Model of T6SS action. OM, outer membrane; PG, peptidoglycan; IM, inner membrane. 4A, Assembly. The first step is a base-plate complex formation that initiates the Hcp tube polymerization. The base-plate complex is probably composed of gp25, VgrG and other T6SS proteins that define a bell-shaped cytoplasmic component (black objects) and periplasmic component (brown objects), which together span the inner membrane, peptidoglycan and outer membrane. The second step is polymerization of the sheath (from VipA/VipB heterodimers) around the Hcp tube in an extended conformation. 4B, Extended T6SS apparatus in extended 'ready to fire' conformation. The membrane distal end may be capped by an unknown protein or VipAB conformational state. 4C, Contraction. Upon an unknown extracellular signal, a conformational change in the base-plate complex triggers sheath contraction that leads to the translocation (secretion) of the VgrG/Hcp tube complex through effector cell membranes and penetration of adjacent target cell membrane. Translocation of additional effector proteins might then follow using the Hcp tube as a conduit. 4D, Disassembly. Contracted sheath is detached and disassembled by ClpV ATPase. VipA/B dimers released are recycled into a new extended T6SS apparatus at either the original or a newly formed base-plate complex. In the absence of target cell penetration (4C), Hcp and VgrG proteins are released into the extracellular space as secreted proteins.

Because the fluorescence microscopic analysis showed that contracted sheath forms from extended sheath, it follows that ClpV may not play a role in T6SS sheath assembly or secretion function; rather, it is responsible for recycling VipA and VipB from contracted T6SS sheath structures through disassembly. The ClpV-mediated disassembly process frequently begins with dislocation of the contracted sheath from the original site of extension (that is, the T6SS base-plate complex) and then continued disassembly in a random fashion throughout the cell cytosol; VipA-sfGFP released by this process is quickly reassembled into new extended sheaths in many cells. Based on these observations, the inventors proposed a detailed model of the dynamic steps in the functional cycle of the T6SS apparatus (FIG. 4). Although analogous to translocation events mediated by contractile phage tails, the proposed T6SS process is different because it occurs in a topologically reversed orientation and compartmentalization (within the cytosol), and further undergoes efficient recycling through the action of other T6SS components such as ClpV. Collectively, the data presented here indicate that energy captured from conformational changes in polymeric structures can rapidly transport proteins through cell membranes.

Methods Summary

*V. cholerae* strains and genetic manipulation has been described previously (Zheng, J. et al., *PLoS ONE* 6, e23876 (2011); Goldberg, S. & Murphy, J. R. *Infect. Immun.* 42, 224-230 (1983); Bina, J. E. & Mekalanos, J. J. *Infect. Immun.* 69, 4681-4685 (2001)). Full-length VipA was fused at its C terminus to either sfGFP or mCherry2 genes (separated by a 3×Ala 3×Gly linker) and expressed from an arabinose-inducible promoter (Guzman, L. M. et al., *J. Bacteriol.* 177, 4121-4130 (1995)) present on either plasmid pBAD24-VipA-sfGFP or pBAD24-VipA-mCherry2. Cells grown to an attenuance at 600 nm ($D_{600}$) of 1.0 in the presence of various concentrations of arabinose were spotted on a thin pad of 1% agarose in PBS and imaged at room temperature. Fluorescence micrographs were captured using microscopes and camera combinations that are described in detail in Methods and image analysis was performed using ImageJ 1.45 software. For electron microscopy, sheath samples prepared as described in Methods were spotted on carbon-coated grids, and stained with 1% uranyl formate. The grids were examined in a JEOL 1200EX transmission electron microscope and images were recorded with an AMT 2 k CCD (charge-coupled device) camera. For ECT, *V. cholerae* cells were grown to $D_{600}$=1.5-2.2, mixed with 10 nm colloidal gold, applied to an electron microscope grid and plunge-frozen in a liquid ethane-propane mixture (Tivol, W. F. et al., *Microsc. Microanal.* 14, 375-379 (2008)). Tilt series were collected using a Polara 300 kV FEG transmission electron microscope equipped with an energy filter (slit width 20 eV) on a lens-coupled 4 k×4 k UltraCam. Pixels on the CCD represented 0.95 nm (×22,500) or 0.63 nm (×34,000) at the specimen level. Leginon (Subway, C. et al. *J. Struct. Biol.* 167, 11-18 (2009)) or UCSF Tomo (Zheng, S. Q. et al. *J. Struct. Biol.* 157, 138-147 (2007)) was used for automatic tilt-series acquisition. Three-dimensional reconstructions were calculated using the IMOD software package (Mastronarde, D. N. *J. Microsc.* 230, 212-217 (2008)) or Raptor (Amat, F. et al. *J. Struct. Biol.* 161, 260-275 (2008)). IMOD (Mastronarde, D. N. *J. Microsc.* 230, 212-217 (2008)) was used to model the centre of the sheath, PEET (Nicastro, D. et al. *Science* 313, 944-948 (2006)) to align and average repeating sub-volumes, and Chimera (Pettersen, E. F. et al. *J. Comput. Chem.* 25, 1605-1612 (2004)) to do isosurface rendering of the sub-volume averages.

Bacterial Strains

*V. cholerae* 2740-80 is a non-toxinogenic El Tor strain isolated in 1980 from a patient in Florida, USA (Goldberg, S. & Murphy, J. R. Infect. Immun. 42, 224-230 (1983)). A streptomycin resistant, lacZ$^-$ derivative of 2740-80 was used as the wild-type parental strain. *E. coli* DH10β and Sm10 γpir were used for cloning and conjugation, respectively. Gentamicin-resistant *E. coli* MG1655 strain was used in bacterial killing assays. *V. cholerae* V52 and its deletion variants were described previously (Zheng, J., Ho, B. & Mekalanos, J. J. *PLoS ONE* 6, e23876 (2011)). Antibiotic concentrations used were streptomycin (100 μg ml$^{-1}$), gentamicin (15 μg ml$^{-1}$) and carbenicillin (100 μg ml$^{-1}$). Luria-Bertani (LB) broth was used for all growth conditions. Liquid cultures were grown aerobically at 37° C.

DNA Manipulations

To generate an in-frame deletion in vipA, vipB, clpV, flgG or VCA0109, the corresponding surrounding DNA was amplified by overlap extension PCR and cloned into pWM91 (Metcalf, W. W. et al. *Plasmid* 35, 1-13 (1996)) for subsequent sacB-mediated allelic exchange as described (Bina, J. E. & Mekalanos, J. J. *Infect. Immun.* 69, 4681-4685 (2001)). Primers were designed such that each deletion resulted in the replacement the entire open reading frame, with the exception of first and last seven codons. Gene deletion was confirmed by PCR with primers outside of the replaced region. For construction of variants of pBAD24, full-length vipA gene was amplified from chromosomal DNA and sfGFP or mCherry2 genes were amplified from plasmids carrying respective genes. Full-length vipA gene, or vipA genes that had been fused with either sfGFP or mCherry2 genes (both separated by a DNA linker encoding 3×Ala 3×Gly), were cloned into plasmid pBAD24. All cloning products were sequence-verified.

Bacterial Killing Assay

*V. cholerae* 2740-80 strains and *E. coli* MG1655 strain were incubated for 14-18 h at 37° C. in LB, then washed in fresh LB and diluted×10 in LB. Attenuance at 600 nm ($D_{600}$) of the culture was adjusted to 0.4 for both *V. cholerae* and *E. coli*. *V. cholerae* was mixed with *E. coli* in a 10:1 ratio and 10 μl of the mixture was spotted on a dry LB agar plate. After 2 and 4 h, bacterial spots were cut out and the cells were re-suspended in 0.5 ml LB. The cellular suspension was serially diluted in LB and 5 μl of the suspensions was spotted on selective plates (gentamicin for *E. coli*, streptomycin 100 μg ml$^{-1}$ *V. cholerae*). Colonies were detected after incubation for approximately 16 h at 30° C.

Cell Fractionation and Immunoblot Analysis

Cells from overnight cultures were washed with fresh LB and diluted 1:100 in 1.5 ml of fresh LB (supplemented with appropriate antibiotics and arabinose to indicated concentrations), cultivated for 2.5-3.0 h to $D_{600}$ about 1.0. Cells were collected by centrifugation at 21,000 g for 1 min and re-suspended in 250 μl SDS-PAGE loading buffer; 15 μl was loaded for western blot analysis. Cell-free supernatants (1.0 ml) were precipitated by 10% trichloroacetic acid for 1 h on ice. Precipitated proteins were collected by centrifugation for 15 min at 21,000 g, washed with 100% acetone and re-suspended in 60 μl SDS-PAGE loading buffer. Twenty microliters was loaded on an SDS-PAGE for western blot analysis. Cell and supernatant protein samples were boiled for 5 min, separated by 10-20% pre-cast polyacrylamide gels (Biorad) and transferred to a nitrocellulose membrane (Biorad). Membrane was blocked by 5% milk in Tris-buffered saline (pH 7.4) containing Tween 0.05% (TBST), incubated with primary peptide antibody for 2 h, washed with TBST, incubated for 1 h with horseradish peroxidase labelled anti-rabbit antibody (Jackson Lab) and washed with TBST; peroxidase was detected by SuperSignal West Pico Chemiluminescent Substrate (Pierce).

Sheath Preparations

Overnight culture was diluted 1:200 into 200 ml of fresh LB and then shaken at 37° C. for 2.5-3.0 h to reach $D_{600}$=1.0-1.5. Cells were cooled on ice, centrifuged for 10 min at 7000 g and lysed in 12 ml lysis buffer (150 mM NaCl, 50 mM Tris, pH 7.4, lysozyme 200 µg ml$^{-1}$, DNase I 50 µg ml$^{-1}$, 1 mM phenylmethylsulphonyl fluoride, 0.5× CelLytic B (Sigma), 1% Triton X-100). Cell lysis was complete after incubation for 5-10 min at 37° C. After cell lysis, samples were cooled on ice and intact cells and cell debris were removed by centrifugation for 15 min at 15,000 g. Cleared lysates were subjected to ultraspeed centrifugation at 150,000 g for 1 h at 4° C. Pellets were re-suspended in 0.5 ml of 50 mM Tris, 150 mM NaCl, pH 7.4, supplemented with protease inhibitor cocktail Complete Mini (Roche) and stored at 4° C. or −20° C. for electron microscopy analysis.

Preparation of Sheath for Mass Spectrometry Analysis

Sheath for mass spectrometry analysis was prepared from an flgG in-frame deletion mutant of the parental 2740-80 strain. Cells were prepared and lysed as described above. To separate the sheath from soluble proteins, the pellet obtained by ultracentrifugation was re-suspended in 12 ml of TN buffer (50 mM Tris, 150 mM NaCl, pH 7.4) and insoluble material removed by a 2 min 15,000 g centrifugation step. The sheath was then collected by sequential ultracentrifugation at 150,000 g for 1 h. The sheath pellet was again re-suspended in 12 ml TN buffer and subjected to another ultracentrifugation step. After three successive ultracentrifugations, samples typically showed only two major bands on a 10-20% SDS-PAGE. The two detectable bands (20 and 50 kDa), and the areas above and below the bands, were cut out from the gel and analysed by tandem mass spectrometry for peptide identity (Taplin Biological Mass Spectrometry Facility, Harvard).

Peptide-Specific Antibodies

Antigen-purified rabbit polyclonal antibodies raised against an Hcp peptide (QSGQPSGQRVHKPF (SEQ ID NO: 16)) and VipA peptide (MSKEGSVAPKERIN (SEQ ID NO: 17)) were obtained commercially (GenScript). Specificity of the antibodies was tested on *V. cholerae* V52 strains expressing or lacking Hcp protein, or *V. cholerae* 2740-80 strains expressing or lacking VipA.

Fluorescence Microscopy

Overnight cultures of *V. cholerae* 2740-80 or V52 strains carrying plasmid pBAD24-VipA-sfGFP or pBAD24-VipA-mCherry2 were diluted 1:100 into fresh LB supplemented with carbenicillin and arabinose (concentrations 0.01%, 0.003% or as indicated) and cultivated for 2.5-3 h to an attenuance of about 1.0. Cells from 100 µl of the culture were re-suspended in 5 µl phosphate buffered saline (PBS), spotted on a thin pad of 1% agarose in PBS, covered with a cover slip and immediately imaged at room temperature.

Fluorescence and phase contrast micrographs were captured using a Nikon TE2000 inverted microscope outfitted with a Nikon Intensilight illuminator, a Coolsnap HQ2 charge-coupled device camera from Photometrics and a CFI Plan Apo DM 100 objective lens (1.4 numerical aperture). The sfGFP images were taken by using the ET-GFP filter set (Chroma 49002). The mCherry2 images were taken by using the ET-mCherry filter set (Chroma 49008). Images were captured using Nikon Elements software. Images were collected every 6 or 10 s, using an exposure time of 100-600 ms for fluorescence and about 10-20 ms for phase contrast. Phase contrast imaging was used to refocus automatically between individual time points. Contrast on images for phase and fluorescence channels was adjusted identically for compared image sets and merged using ImageJ 1.45 software. Small movement of whole field in time was corrected by registering individual frames using StackReg plugin for ImageJ ('Rigid Body' transformation). The pixel-size was 60 nm.

High-frame-rate fluorescent images were collected with a Nikon Ti-E inverted motorized microscope equipped with a ×100 Plan Apo NA 1.4 objective lens and the Perfect Focus System for continuous maintenance of focus. VipA-sfGFP fluorescence was excited using a Prior Lumen200Pro metal halide epi-fluorescence light source, selected with an ET490/20× filter (Chroma) and collected with an ET535/30m filter (Chroma). Two different cameras and acquisition settings were used to collect images. A Hamamatsu ORCA-R2 cooled CCD camera was used to acquire images every 118 ms (exposure time 50 ms, with continuous illumination). A Hamamatsu ORCA-Flash2.8 cooled CMOS camera was used to acquire images every 20 ms (no analogue gain) or 5 ms (8× on-chip analogue gain) under continuous illumination light. Both cameras were controlled with Molecular Devices MetaMorph version 7.7 software. Contrast was adjusted identically for compared image sets. All image processing and analyses were done using ImageJ 1.45 software. The pixel size was 67 nm for the ORCA-R2 and 78 nm for the ORCA-Flash2.8 camera.

Plunge-Freezing

For ECT, *V. cholerae* 2740-80 wild-type and mutant strains were grown aerobically at 37° C. in LB medium. A 5 ml overnight-culture was diluted 1000-fold and grown to $D_{600}$=1.5-2.2. Copper/rhodium electron microscopy grids (R2/2, Quantifoil) were glow-discharged for 1 min. A 20×-concentrated bovine serum albumin-treated solution of 10 nm colloidal gold (Sigma) was added to the sample (1:4 v/v) immediately before plunge freezing. A 4 µl droplet of the mixture was applied to the electron microscopy grid, then automatically blotted and plunge-frozen into a liquid ethane-propane mixture (Tivol, W. F. et al., *Microsc. Microanal.* 14, 375-379 (2008)) using a Vitrobot (FEI Company) (Iancu, C. V. et al. *Nature Protocols* 1, 2813-2819 (2006)). The grids were stored in liquid nitrogen.

Negative Stain Electron Microscopy

Samples were incubated on carbon-coated grids for about 1 min. Grids were washed in water and stained by 1% uranyl formate. The grids were examined in a JEOL 1200EX transmission electron microscope and images were recorded with an AMT 2 k CCD camera.

Electron Cryotomography

Tilt series were collected using a Polara 300 kV FEG transmission electron microscope (FEI Company) equipped with an energy filter (slit width 20 eV; Gatan) on a lens-coupled 4 k×4 k UltraCam (Gatan). Pixels on the CCD represented 0.95 nm (×22,500) or 0.63 nm (×34,000) at the specimen level. Typically, tilt series were recorded from −60° to +60° with an increment of 1° at 10 µm under-focus. The cumulative dose of a tilt-series was 180-220 electrons Å$^{-2}$ (for whole cells) or 80-100 electrons Å$^{-2}$ (for sheath preparations). Leginon (Subway, C. et al. *J. Struct. Biol.* 167, 11-18 (2009)) or UCSF Tomo (Zheng, S. Q. et al. *J. Struct. Biol.* 157, 138-147 (2007)) was used for automatic tilt-series acquisition. Three-dimensional reconstructions were calculated using the IMOD software package (Mastronarde, D. N. *J. Microsc.* 230, 212-217 (2008)) or Raptor (Amat, F. et al. *J. Struct. Biol.* 161, 260-275 (2008)).

Sub-Tomogram Averaging

IMOD (Mastronarde, D. N. *J. Microsc.* 230, 212-217 (2008)) was used to model the centre of the sheath. The program addModPts was run to fill in model points every 8 nm along the tube axis. The PEET software package (Nicastro, D. et al. *Science* 313, 944-948 (2006)) was used to align and average repeating sub-volumes. Isosurface rendering of the sub-volume averages was done with Chimera (Pettersen, E. F. et al. *J. Comput. Chem.* 25, 1605-1612 (2004)).

---

The invention claimed is:

1. An isolated tubular structure comprised of a plurality of molecules of a VipA polypeptide of SEQ ID NO: 1 and a plurality of molecules of a VipB polypeptide of SEQ ID NO: 3,
   wherein the VipA polypeptide molecules assemble with the VipB polypeptide molecules to form the tubular structure,
   wherein the VipA polypeptide or the VipB polypeptide further comprises a polypeptide of interest as a fusion polypeptide, and
   wherein the tubular structure displays a plurality of molecules of said polypeptide of interest.

2. A method for making a vaccine, the method comprising: combining an isolated tubular structure of claim 1 with a pharmaceutically acceptable carrier.

3. The isolated tubular structure of claim 1, wherein the displayed polypeptide has a conformation substantially similar to the folding pattern of the protein of interest when not displayed in this manner.

4. The isolated tubular structure of claim 1, wherein the displayed polypeptide is more immunogenic than the protein of interest when not displayed in this manner.

5. The isolated tubular structure of claim 1, wherein the plurality of molecules of the polypeptide of interest are displayed as a regular, repetitive structure.

6. The isolated tubular structure of claim 1, wherein the polypeptide of interest comprises a viral protein, a bacterial protein, a fungal protein or a tumor protein.

* * * * *